United States Patent [19]

Bodor

[11] Patent Number: 4,703,042
[45] Date of Patent: Oct. 27, 1987

[54] ORALLY ACTIVE HEPARIN SALTS CONTAINING MULTIVALENT CATIONIC UNITS

[76] Inventor: Nicholas S. Bodor, 7211 SW. 97th La., Gainesville, Fla. 32608

[21] Appl. No.: 808,689

[22] Filed: Dec. 17, 1985

Related U.S. Application Data

[63] Continuation of Ser. No. 612,593, May 21, 1984, abandoned.

[51] Int. Cl.$^4$ ................ A61K 31/725; A61K 31/715; C08B 37/10
[52] U.S. Cl. .................................... 514/56; 514/58; 514/822; 536/21
[58] Field of Search .......................... 514/56, 58, 822; 536/21

[56] References Cited

U.S. PATENT DOCUMENTS

| | | | |
|---|---|---|---|
| 3,506,642 | 4/1970 | Koh et al. | 536/21 |
| 3,617,344 | 11/1971 | Leininger et al. | 514/56 |
| 3,835,112 | 9/1974 | Mardiguian et al. | 536/21 |
| 3,891,622 | 6/1975 | Mardiguian et al. | 536/21 |
| 4,020,160 | 4/1977 | Bernstein et al. | 514/58 |
| 4,247,535 | 1/1981 | Lewis et al. | 514/58 |
| 4,415,490 | 11/1983 | Joh | 536/21 |
| 4,510,135 | 4/1985 | Teng | 536/21 |

FOREIGN PATENT DOCUMENTS

| | | |
|---|---|---|
| 326127 | 11/1975 | Austria . |
| 0036145 | 9/1981 | European Pat. Off. ............ 424/183 |
| 2128377 | 12/1971 | Fed. Rep. of Germany ...... 424/183 |
| 2492259 | 4/1982 | France ................................. 424/183 |
| 0035781 | 4/1978 | Japan ................................... 424/183 |
| 60-51122 | 3/1985 | Japan . |
| 85/05362 | 12/1985 | PCT Int'l Appl. . |
| 2065663 | 4/1979 | United Kingdom . |

OTHER PUBLICATIONS

Hara et al., . . . Polyelectrolyte Complex of Heparin with . . . Poly(Vinyl Alcohol), Chem. Abstracts 88:121874p (1978).

*Primary Examiner*—J. R. Brown
*Assistant Examiner*—John W. Rollins, Jr.
*Attorney, Agent, or Firm*—Mary Katherine Baumeister

[57] ABSTRACT

The invention provides novel orally active salts of the formula

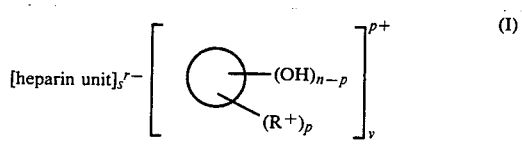

in which ◯ is the skeleton of a polyol, n is the number of OH's in the polyol (3 to 24); p is $\geq 3$ and $\leq n$; r is the available valence of the heparin unit and $\geq 3$ and $\leq 7$; sr is equal to pv; and R+ is

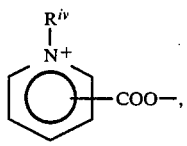 (a)

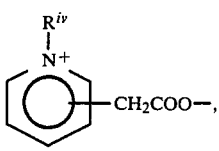

(b)

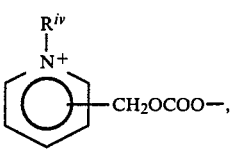

(c)

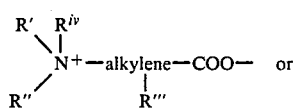

(d)

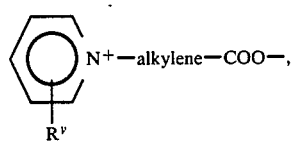

(e)

in which $R^{iv}$ is $C_1$–$C_3$ alkyl; R' and R" are $C_1$–$C_7$ alkyl, the same or different, or combined so that —NR'R" represents the residue of a saturated monocyclic secondary amine; R''' is identical to the corresponding portion of a natural amino acid; the alkylene groups contain 1 to 3 carbon atoms; and $R^v$ is H, —CONH$_2$ or —COO($C_1$–$C_7$ alkyl). The salts are stable lipoidal "ion pairs" or complexes which can be absorbed through the gastrointestinal wall and which slowly release heparinic acid to achieve long-lasting anticoagulant activity. Novel quaternary salts which are intermediates to the heparin salts of the invention are also disclosed.

53 Claims, 3 Drawing Figures

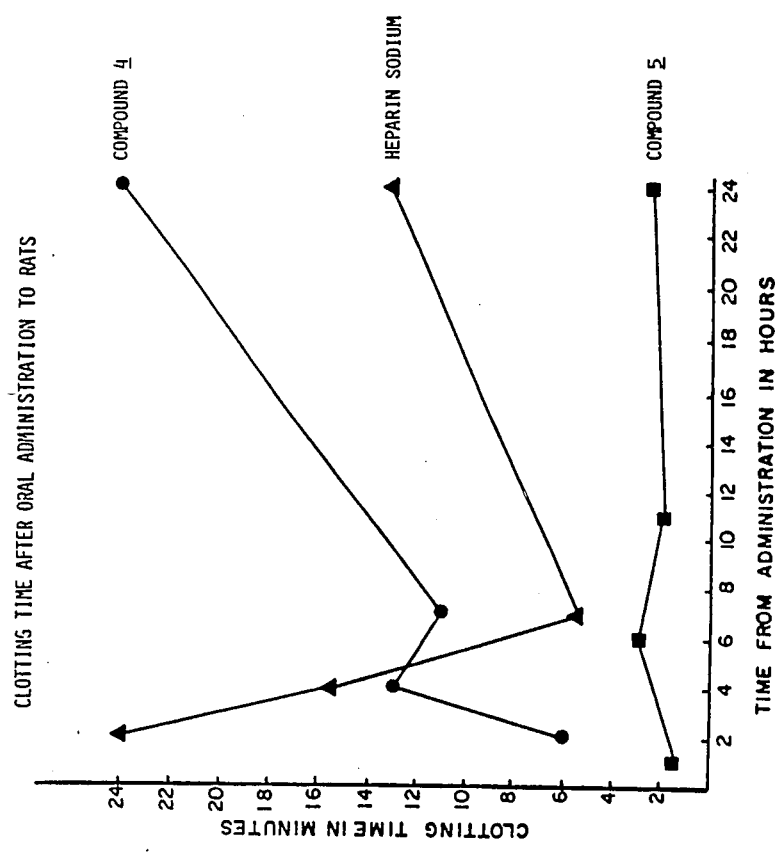

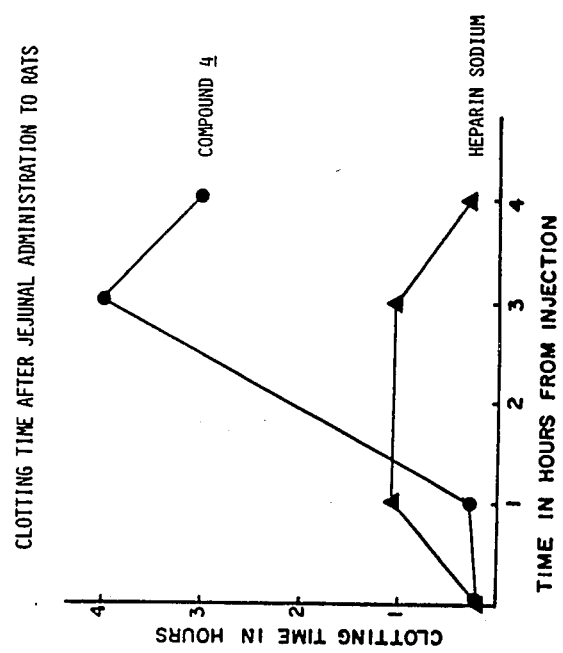

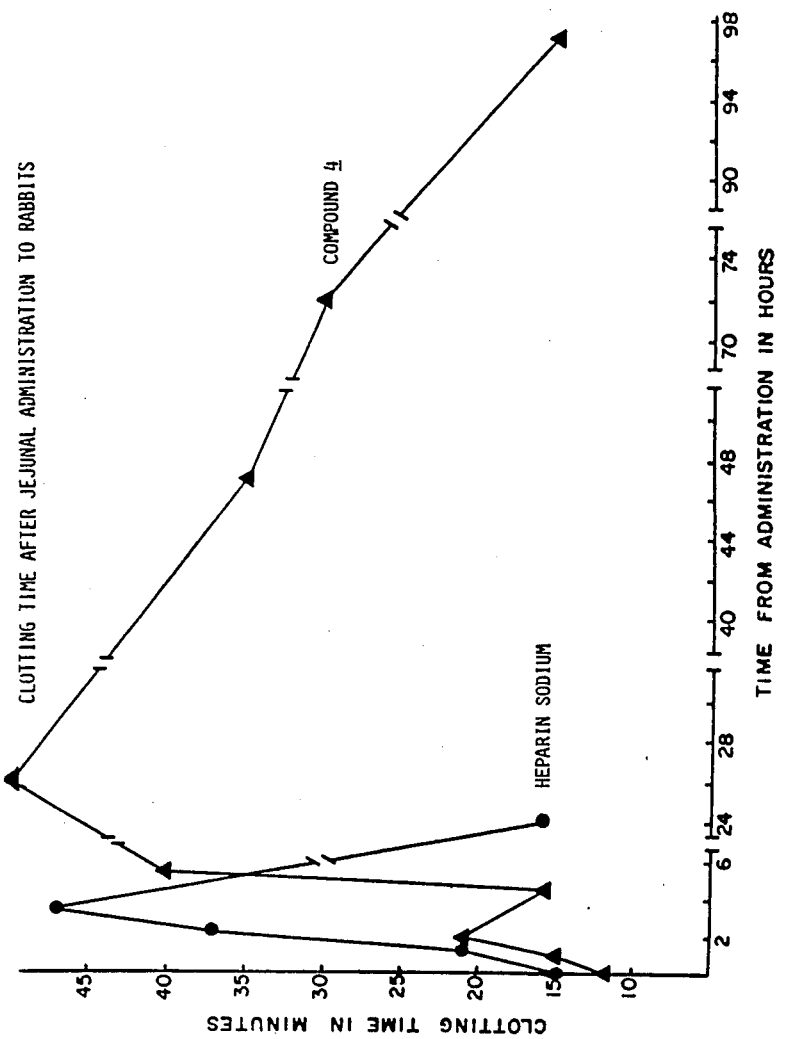

ORALLY ACTIVE HEPARIN SALTS CONTAINING MULTIVALENT CATIONIC UNITS

This application is a continuation of application Ser. No. 612,593, filed May 21, 1984, now abandoned.

FIELD OF THE INVENTION

The present invention provides novel orally active salts of polyanionic heparinic acid with selected polycationic materials. The salts are stable lipoidol "ion-pairs" which can be absorbed through the gastrointestinal wall and which slowly release heparinic acid to achieve long-lasting anticoagulant activity.

BACKGROUND OF THE INVENTION

Since the initial reports about heparin [Howell et al, Am. J. Physiol. 47, 328 (1918)] and bishydroxycoumarin or dicumarol [Link, Harvey Lect., 39, 162-216(1944)], anticoagulants have become the object of extensive biological investigation. Heparin is still considered by many as the drug of choice, despite the fact that it is not well absorbed orally and must be administered by a parenteral route. Toxic side effects are uncommon, but parenteral administration, whether as intermittent injections or continuous infusion, precludes its long term use. Therapy employing the clinically used oral anticoagulants, on the other hand, is difficult to control between desired limits because of the considerable variability in their rates of metabolism under differing conditions. In addition to undesirable delay in onset of activity after administration, drug interaction problems and side effects make the oral anticoagulants which are now available poor substitutes for heparin itself.

The possibility of administering heparin by routes other than injection while obtaining results comparable to those obtained by injection has aroused the interest of many investigators. See, for example, Windsor et al, Nature, London, 190, 263 (1961); Teow Yan Koh, U.S. Pat. Nos. 3,482,014, 3,510,561 and 3,548,052; and Teow Yan Koh et al, U.S. Pat. Nos. 3,506,642 and 3,577,534. Notably, orally active heparin salts and complexes have been described in the patent literature, e.g. amines, amides (the aforementioned Teow Yan Koh patents) and acid salts such as Na, K, Li etc. (the aforementioned Teow Yan Koh et al patents). Attempts have also been made to enhance oral absorption using sulfoxides and sulfones.

Nevertheless, serious need exists in this art for improved oral delivery of heparin.

SUMMARY AND OBJECTS OF THE INVENTION

Accordingly, a major object of the present invention is to provide improved delivery of heparin by the oral route. Another object of this invention is provide a form a heparin which will be readily absorbable from the intestine. Another object of this invention is to provide an orally active form of heparin which will be highly stable and which will have a long duration of anticoagulant activity as compared to heparin sodium. These and other objects are achieved by the use of novel orally active salts of polyanionic heparinic acid with selected polycationic materials. These salts are stable lipoidol "ion-pairs" which can be absorbed through the gastrointestinal wall and which slowly release heparinic acid to achieve long-lasting anticoagulant activity.

BRIEF DESCRIPTION OF THE DRAWINGS

FIG. 1 is a graph plotting the amount of time required for clotting, in minutes, against the time elapsed since oral administration to rats, in hours, for Compound 4 [heparin inositol hexa-(1-methyl-3-pyridiniumcarboxylate) salt], Compound 5 [heparin N,N-dimethyl-N-dodecyl-N-($\beta$-hydroxy)ethylammonium salt] and heparin sodium;

FIG. 2 is a graph plotting the amount of time required for clotting, in hours, against the time elapsed since jejunal administration to rats, in hours, for Compound 4 [heparin inositol hexa-(1-methyl-3-pyridiniumcarboxylate) salt] and heparin sodium; and FIG. 3 is a graph plotting the amount of time required for clotting, in minutes, against the time elapsed since jejunal administration to rabbits, in hours, for Compound 4 [heparin inositol hexa(1-methyl-3-pyridiniumcarboxylate) salt] and heparin sodium.

DETAILED DESCRIPTION OF THE INVENTION

"Heparin", or heparinic acid, as used herein refers to a mucopolysaccharide present in mammalian tissue which has strong anticoagulant activity. The polysaccharide is a dextrorotatory, highly sulfated, negatively charged, strongly acidic polymer mixture of disaccharides or the corresponding tetrasaccharides. The precise chemical formula, structure and molecular weight are not yet fully elucidated and appear to vary with biological source. Goodman and Gilman's The Pharmacological Basis of Therapeutics, sixth edition, Macmillian Publishing Co., Inc., New York, New York, Chapter 58, pp. 1348-1351, indicates that heparin has an average molecular weight of 15,000 daltons and that commercial heparin is composed of polymers of two repeating disaccharide units, namely, a D-glucosamine-L-iduronic acid unit and a D-glucosamine-D-glucuronic acid unit. According to Goodman and Gilman, most samples of heparin sodium contain from 8 to 15 repeats of each unit, although they may not be in equal proportions. A structure for heparin sodium as depicted by Goodman and Gilman is shown below. See also Cutting's Handbook of Pharmacology, seventh edition, ed. T. Z. Csáky, M. D. and Byron A. Barnes, Ph.D., Appleton-Century-Crofts, Norwalk, Conn., Chapter 27, pp. 318-319; The Merck Index, tenth edition, Merck & Co., Inc., Rahway, N.J., 1983, pages 672-673; and The Condensed Chemical Dictionary, eighth edition, revised by Gessner G. Hawley, Van Nostrand Reinhold Company, New York, page 436.

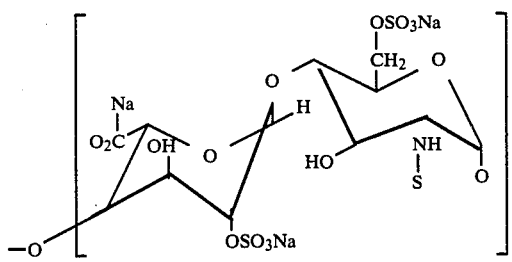

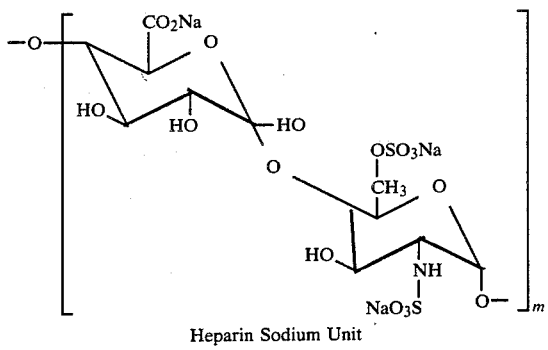

Heparin Sodium Unit

The chain lengths and potency of heparin samples vary widely. Consequently, heparin is prescribed on a unit basis. The U.S.P. unit of heparin is the amount required to prevent 1.0 ml of citrated sheep plasma from clotting for one hour after addition of 0.2 ml of a 1:100 calcium chloride solution. Heparin Sodium, U.S.P., must contain at least 120 U.S.P. units/mg.

The heparin salts or complexes of the present invention can be represented by the structural formula

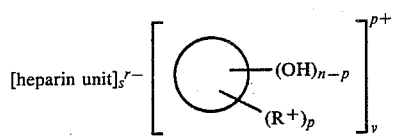
(I)

wherein ◯ is the skeleton of a polyol, said skeleton being the portion of said polyol which would remain after removal of all hydroxy substituents therefrom; n is a number from 3 to about 24 which represents the total number of hydroxy groups in said polyol; p is a number $\leq 3$ and $\geq n$; r is the available valence of the heparin unit and is $\geq 3$ and $\leq 7$; s is the number which when multiplied by r is equal to pv; v is the number which when multiplied by p is equal to rs; $R^+$ is

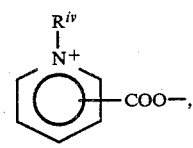  (a)

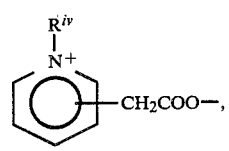  (b)

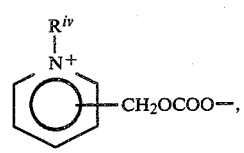  (c)

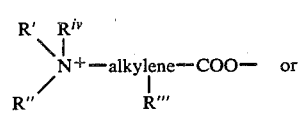  (d)

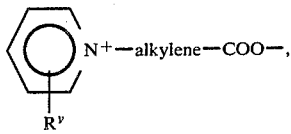  (e)

wherein the —COO—, —CH$_2$COO—, —CH$_2$OCOO— and $R^v$ ring substituents can each be in the 2-, 3- or 4-position of the pyridinium ring; $R^{iv}$ is C$_1$–C$_3$ alkyl; R′ and R″, which can be the same or different, are each C$_1$–C$_7$ alkyl, or R′ and R″ are combined with the adjacent nitrogen atom such that

represents the residue of a saturated monocyclic secondary amine; R‴ is a radical identical to the corresponding portion of a natural amino acid; the alkylene groups can be straight or branched and contain 1 to 3 carbon atoms; and $R^v$ is H, —CONH$_2$ or —COO(C$_1$–C$_7$ alkyl).

The expression "[heparin unit]" as used herein is intended to indicate the basic tetrasaccharide unit which makes up heparin sodium itself except that from 3 to 7 of the sodium ions are removed, leaving a polyanion having an available or effective valence of from 3 to 7 which can then be "ion-paired" to the desired polycations to form the salts of formula (I). While a typical heparin sodium tetrasaccharide unit would contain one each of the D-glucosamine-L-iduronic acid disaccharide unit and the D-glucosamine-D-glucuronic acid disaccharide unit, the exact identity of the tetrasaccharide unit will vary with source, as already explained hereinabove, as will the number of repeats of each disaccharide unit (typically 8 to 15 of each, but not necessarily in equal proportion) in a given sample. Thus, for example, a given heparin sodium tetrasaccharide unit may well be composed of two D-glucosamine-L-iduronic acid disaccharide units or two D-glucosamine-D-glucuronic acid disaccharide units rather than one of each disaccharide, and a particular heparin sample may well contain tetrasaccharide units of each of these three types. The expression "[heparin unit]" as used herein is intended to encompass any such units, save of course for the absence of some or all of the sodium cations, as explained above; in any given multiplet of this invention, the heparin units will be identical to those in the heparin sodium sample from which the salt is derived except for the difference in sodium content.

The expression "polyol" as used herein is intended to indicate a monosaccharide, oligosaccharide, C$_5$–C$_{18}$ alicyclic polyhydroxy compound or C$_3$–C$_{15}$ aliphatic polyhydroxy compound, i.e. a compound of the formula

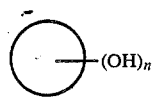
(II)

wherein ◯ and n are defined as before. The hydroxy groups are usually situated on the carbon atoms in the polyol backbone or skeleton, but in some cases are located on pendant methyl radicals, particularly in the case of the monosaccharides and oligosaccharides.

When the polyol is an aliphatic polyol, it is preferably a $C_3$–$C_8$ alkyl polyol such as glycerol, erythritol(tetrahydroxybutane) or 1,2,6-trihydroxyhexane.

When the polyol is an alicyclic polyol, it is preferably a $C_5$–$C_{10}$ cycloalkyl or fused fully hydrogenated aromatic polyol (e.g. a cyclohexane or decahydronaphthalene polyol). A particularly preferred cycloalkyl polyol is inositol, a non-toxic substance which is widely distributed in plants and microorganisms. Inositol, which has the empirical formula $C_6H_{12}O_6$, has a number of possible stereoisomers. Shown below is the structure for cis-1,2,3,5-trans-4,6-cyclohexanehexol, the prevalent natural form:

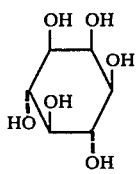

When the polyol is a monosaccharide, it is preferably a pentose, hexose or heptose. Suitable such simple sugars include aldopentoses such as ribose, arabinose, xylose and lyxose; ketopentoses such as ribulose and xylulose; aldohexoses such as glucose, galactose and mannose; ketohexoses such as fructose, sorbose and tagatose; and ketoheptoses such as mannoheptulose and sedoheptulose. Structures for some typical monosaccharides contemplated by the present invention are as follows:

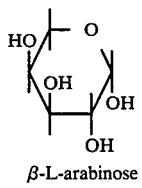 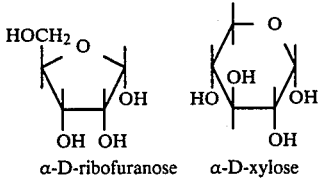

β-L-arabinose   α-D-ribofuranose   α-D-xylose

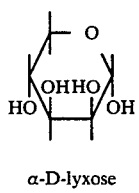 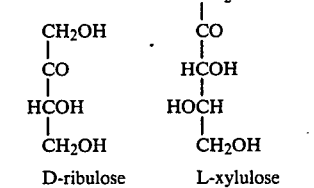

α-D-lyxose   D-ribulose   L-xylulose

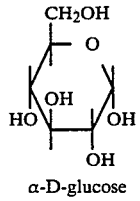 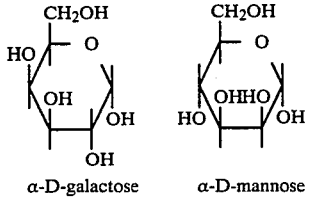

α-D-glucose   α-D-galactose   α-D-mannose

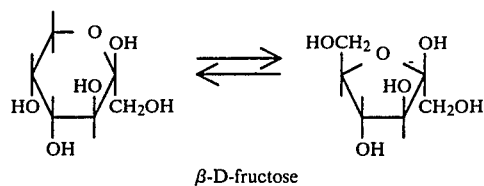

β-D-fructose

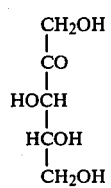 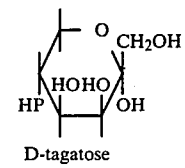

L-sorbose   D-tagatose

When the polyol is an oligosaccharide, i.e. a carbohydrate which yields 2 to 8 monosaccharide units upon acid hydrolysis, it is preferably a disaccharide, a trisaccharide or a cyclodextrin. Representative disaccharides are sucrose, lactose and maltose. A representative trisaccharide is raffinose. The cyclodextrins, or cycloamyloses, are homogeneous cyclic α-(1→4) linked D-glucopyranose units. α-Cyclodextrin contains 6 units, β-cyclodextrin contains 7 and γ-cyclodextrin contains 8. Structures for representative oligosaccharides contemplated by the present invention are as follows:

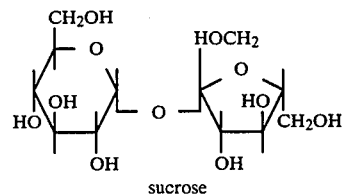

sucrose

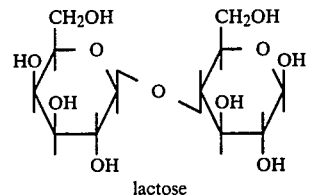

lactose

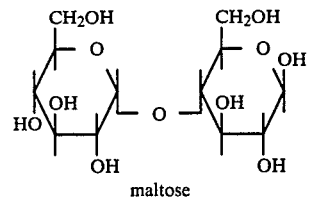

maltose

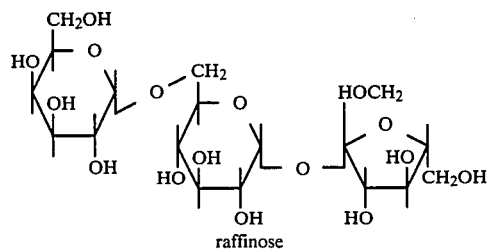

raffinose

-continued

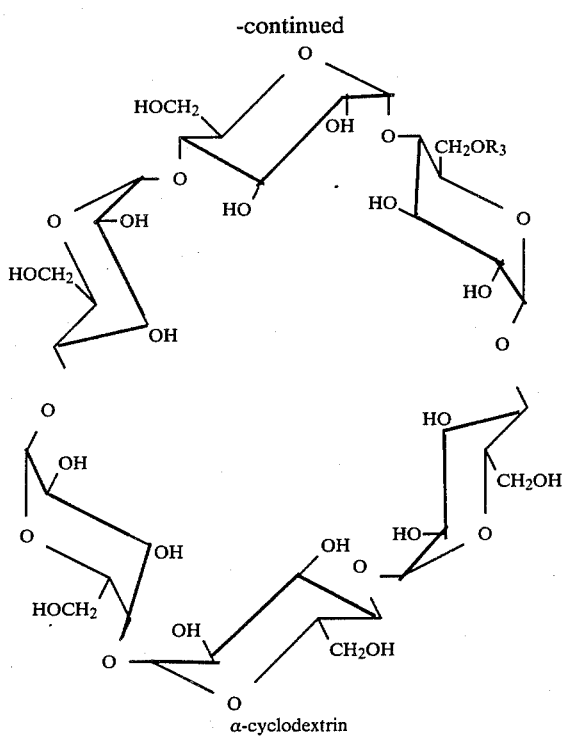

α-cyclodextrin

The expression "C₁-C₃ alkyl" and "C₁-C₇ alkyl" as used herein indicate straight or branched-chain groups containing the indicated number of carbon atoms, e.g. methyl, ethyl, propyl, isopropyl, as well as the higher homologues when the alkyl radical contains more than 3 carbon atoms, e.g. butyl, pentyl, hexyl and heptyl and the corresponding branched-chain isomers, e.g. isobutyl and tert-butyl.

The expression "R''' is a radical identical to the corresponding portion of a natural amino acid" is believed to be self-explanatory. Thus, for example, R''' can be hydrogen, as in glycine; methyl, as in alanine; —CH(CH₃)₂, as in valine; —CH₂—CH(CH₃)₂, as in leucine;

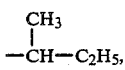

as in isoleucine;

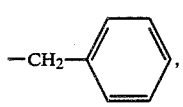

as in phenylalanine;

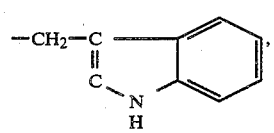

as in tryptophan; —CH₂OH, as in serine; —CHOH—CH₃, as in threonine; —(CH₂)₂—SCH₃, as in methionine; —CH₂—CONH₂, as in asparagine; —CH₂CH₂—CONH₂, as in glutamine;

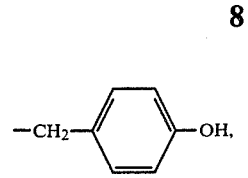

as in tyrosine; —CH₂SH, as in cysteine; —CH₂COOH, as in aspartic acid; and —CH₂CH₂COOH, as in glutamic acid.

When R' and R'' are combined with the adjacent nitrogen atom such that

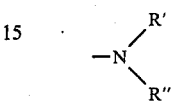

represents the residue of a saturated monocyclic secondary amine, such monocycles preferably have 5 to 7 ring atoms, optionally contain another hetero ring atom (—O—, —S— or —N—) in addition to the indicated nitrogen atom, and optionally bear one or more substituents such as methyl. Illustrative of residues of saturated monocyclic secondary amines which are encompassed by the

term are morpholino, 1-pyrrolidinyl, perhydro-1,2,4-oxathiazin-4-yl, 1- or 4-piperazinyl, 4-methyl-1-piperazinyl, piperidino, hexamethyleneimino, 2-methyl-1-pyrazolidinyl, 1- or 2-pyrazolidinyl, 3-methyl-1-imidazolidinyl and 1- or 3-imidazolidinyl.

When R⁺ in formula (I) is structure (a), $R^{iv}$ is preferably methyl and the —COO— group is preferably located in the 3-position. When R⁺ in formula (I) is structure (b), $R^{iv}$ is preferably methyl and the —CH₂COO— group is preferably located in the 3-position. When R⁺ in formula (I) is structure (c), $R^{iv}$ is preferably methyl and the —CH₂OCOO— group is preferably located in the 3-position. When R⁺ in formula (I) is structure (d), preferably R' and R'' are both methyl or both ethyl, or R'R''N- represents morpholino, piperidino, 1-pyrrolidinyl or 1-piperazinyl; $R^{iv}$ is preferably methyl; alkylene is preferably

and R''' is preferably H, —CH₃, —CH(CH₃)₂, —CH₂—CH(CH₃)₂,

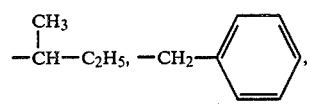

—(CH₂)₂—SCH₃, —CH₂—CONH₂, —CH₂CH₂—CONH₂ or

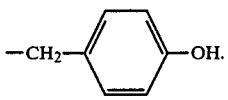

When R+ in formula (I) is structure (e), alkylene is preferably —CH₂CH₂—; and R$^v$ is preferably H or —CONH₂. Structures (a), (d), and (e) are particularly preferred, especially when one or more of the structural variables there are as set forth in this paragraph.

In formula (I), it is also preferred that p be equal to n so that n minus p equals zero, in which case the heparin salts can be represented by the formula

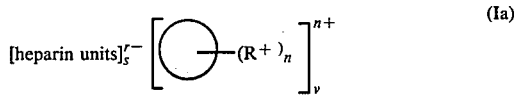

wherein the structural variables are as generally defined above. Especially preferred salts of formula (Ia) are those in which one or more of the structural variables are selected from the preferred variables set forth in the preceding paragraph.

It is also preferred that there be at least four R+ groups in the salts of formulas (I) and (Ia). Moreover, it is preferred that r in formulas (I) and (Ia) be 5, 6 or 7.

In one preferred embodiment of this invention, in formula (I), ○ is the skeleton of inositol, n is 6 and p is 6. In one especially preferred embodiment of this invention, in formula (I), ○ is the skeleton of inositol, n is 6, p is 6, v is 5, r is 5 and s is 6.

The "ion-paired" complex or salt formed by this interaction of the heparinic acid anion and the quaternary ammonium cation is expected to be hydrophobic and absorbable from the intestine. The strong ionic interaction is expected to give high stability to the ion pairs. The complexity and high hydrophobicity of the products are expected to reflect slow dissociation, whether before, after of during absorption and, hence, slow release of heparinic acid and longer duration of action.

The salts of formula (I) can be prepared by a variety of conventional synthetic methods. One general method comprises coupling the selected polyol of formula (II) hereinabove with a quaternary acid salt of the formula

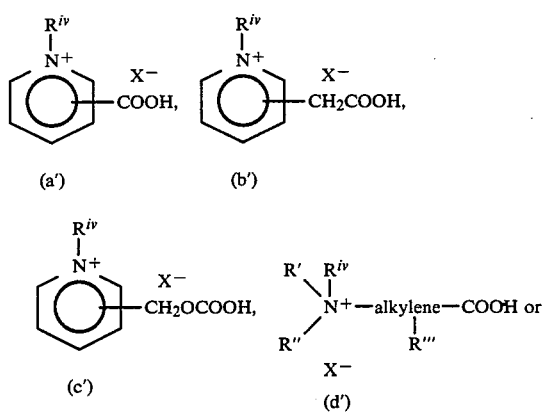

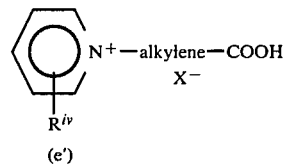

wherein the structural variables are as hereinbefore defined in connection with structures (a), (b), (c), (d) and (e), respectively, and X⁻ is the anion of a pharmaceutically acceptable organic or inorganic acid. The coupling, or esterification, is typically carried out in the presence of a suitable coupling agent such as dicyclohexylcarbodiimide, in an appropriate organic solvent, using excess acid reactant so that as many as possible of the hydroxy groups in the polyol will be esterified. Other esterification procedures will be readily apparent to the skilled organic chemist, e.g. use of a mixed anhydride. The resultant novel intermediates can be represented by the structural formula

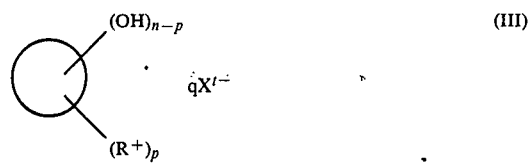

wherein ○, n, p and R+ are as defined in connection with formula (I); X⁻ is the anion of a pharmaceutically acceptable acid (e.g. an inorganic acid such as hydrochloric acid, sulfuric acid or hydrobromic acid, or an organic acid such as acetic acid, oxalic acid, succinic acid, maleic acid, fumaric acid, malic acid, tartaric acid, citric acid, malonic acid, methanesulfonic acid or benzoic acid); t is the valence of the acid anion and q is the number which when multiplied by t is equal to p; thus, when X$^{t-}$ is a monovalent anion, q will be equal to p; when the anion is divalent, q will be equal to p/2; and when the anion is trivalent, q will be equal to p/3. Further, it is preferred that p be equal to n so that n−p=0, the quaternary intermediate in such case being represented by the formula

wherein the structural variables are defined as above. Preferred polycationic quaternary intermediates are those which lead to the preferred formula (I) ion pairs already discussed above. Especially preferred formula (III) intermediates are derived from non-toxic naturally-occurring substances, and are themselves non-toxic and will be metabolixed to non-toxic moieties. Presently preferred quaternaries can be considered to be derived from inositol as the polyol and trigonelline (which occurs in the seeds of many plants and is excreted in the urine after taking nicotinic acid) and betaine (which is widely distributed in plants and animals) as the quaternized acid portion. The structures of trigonelline and betaine are as follows:

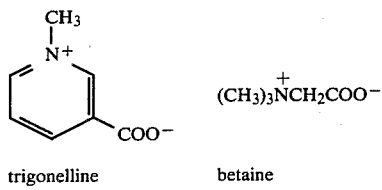

trigonelline   betaine

The novel quaternary ester intermediates of formula (III) are then conveniently reacted with heparin sodium, in aqueous medium, to afford the desired salts of formula (I). Typically, equivalent amounts of reactants are employed in this step. As many sodium ions as possible will be replaced with quaternary ester groupings in this step, i.e. at least 3, but more typically 5 to 7. While not wishing to be bound by this interpretation, it is believed that when heparin sodium has the structure depicted earlier in this specification, of the seven sodium cations per tetrasaccharide unit, those $Na^+$'s associated with the $CO_2^-$ groupings are more tightly held than those associated with $SO_3^-$ groupings and are consequently easier to replace with the instant cationic entities; and that generally at least the five $SO_3^-$ anions will become associated with the new cations.

Nevertheless, other synthetic routes to the instant multiplets are presently preferred. Thus, the presently preferred process for the preparation of the salts of formula (I) wherein $R^+$ is structure (a), (b), (c) or (d) is to first couple the selected polyol of formula (II) with a tertiary acid of the formula

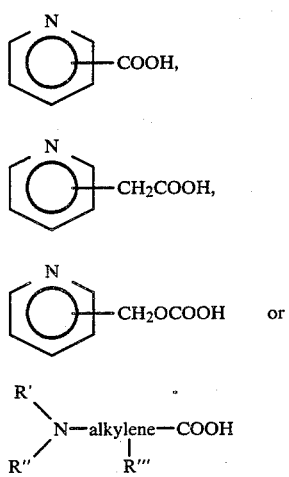

or the corresponding acid halide (e.g. chloride) or anhydride, wherein the structural variables are as previously defined in connection with structures (a), (b), (c) and (d), respectively. When the esterifying agent is an acid, the process is typically carried out in the presence of a suitable coupling agent such as dicyclohexylcarbodiimide (DCC) in an appropriate organic solvent such as pyridine, acetonitrile or dichloromethane, the solvent of choice depending upon the particular reactants employed. When the esterifying agent is an acid anhydride (prepared, for example, by reacting the corresponding acid with phosgene), an organic solvent such as pyridine can be employed. When the esterifying agent is an acid chloride (prepared, for example, by reacting the corresponding acid with a chlorinating agent such as thionyl chloride or phosphorus oxy-chloride), choice of solvent will vary not only with the particular reactants used but also with whether or not the acid chloride is isolated prior to the esterification step. For example, when the acid chloride is isolated as the hydrochloride, then that salt can be conveniently reacted with the polyol in chloroform. On the other hand, if the acid is first reacted with $POCl_3$ and the polyol subsequently added to the reaction mixture, both steps can be conveniently conducted in pyridine. Whatever the esterifying agent, it will be used in excess so as to esterify as many of the hydroxy groups in the polyol as possible, e.g. when inositol is used as the polyol, a six-fold or greater excess of monocarboxylic acid or acid chloride will be used (i.e. 6 or more moles of acid or acid chloride per mole of polyol). When a starting acid of structure (d") or the corresponding acid chloride or anhydride is used, the R''' group therein preferably does not contain free hydroxy, thiol or carboxy functions which could interfere with coupling with the polyol structure. However, such functions can be conveniently protected, if desired, e.g. with ester groupings (for example, $C_1$–$C_7$ lower alkyl esters) prior to acylation and subsequently deprotected. Also, carboxy functions contained in the R''' grouping need not be protected if the polyol contains sufficient hydroxy groups; e.g., if R''' is —$CH_2CH_2COOH$, then each amino acid could combine with two hydroxy groups and at least six hydroxy groups would need to be present in the polyol in order to give an acylated derivative in which there are sufficient R groups, i.e. at least three.

The products of the above-described first step of the presently preferred process for the preparation of the formula (I) salts in which $R^+$ is structure (a), (b), (c) or (d) can be represented by the structural formula $$\bigcirc \begin{array}{c} (OH)_{n-p} \\ R_p \end{array} \quad (IV)$$

wherein $\bigcirc$, n and p are as defined in connection with formula (I) and R is the residue of one of the aforementioned acids (a") to (d"), i.e. R is

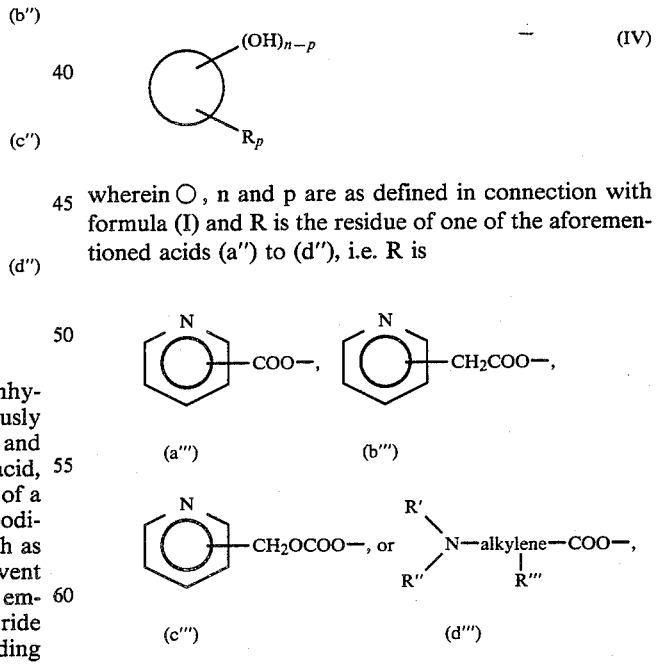

wherein the structural variables are as defined in connection with structures (a), (b), (c) and (d) hereinabove. Preferably, p is equal to n in formula (IV) so that n−p=0, the acylate in such case being represented by the formula

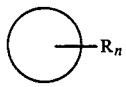 (IVa)

wherein R and n are defined as above.

The acylates of formula (IV) are then quaternized typically by treatment with a $C_1$-$C_3$ alkyl halide, $R^{iv}$—Hal, preferably methyl iodide, in an appropriate solvent such as dimethylformamide. Preferably, the formula (IV) acylate is heated (e.g. at about 50° C.) with excess of the alkylating agent in dimethylformamide for at least forty-eight hours. The resultant quaternized acylate wherein the anion is $I^-$ or other halide can then be subjected to anion exchange when an anion is desired which is different from the one obtained; such anion exchange may be accomplished via an anion exchange resin or, more conveniently, by use of the method of Kaminski et al, Tetrahedron, Vol. 34, pp. 2857–2859 (1978). According to the Kaminski et al method, a methanolic solution of a pharmaceutically acceptable organic or inorganic acid HX will react with a quaternary ammonium halide to produce the methyl halide and the corresponding quaternary .X salt. The quaternization and when desired the subsequent anion exchange afford the novel chemical intermediates of formula (III) hereinabove wherein $R^+$ is structure (a), (b), (c) or (d) as defined with formula (I). Again, the preferred compounds of formula (III) are as discussed in connection with the first synthetic route discussed above. And again, those novel intermediates can then be reacted with heparin sodium as already described above to afford the corresponding heparin salts of formula (I).

A presently preferred process for the preparation of the salts of formula (I) wherein $R^+$ is structure (e) utilizes a starting material of the formula

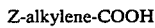 Z-alkylene-COOH (V)

or

 Z-alkylene-COY (VI)

wherein Z is Cl, Br or I; the alkylene group can be straight or branched and contains 1 to 3 carbon atoms; and Y is Cl or Br. The formula (V) or (VI) starting material is first reacted with a polyol of formula (II) above to afford an intermediate polyester of the formula

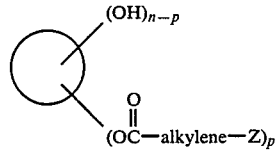 (VII)

wherein ◯, n and p are as defined in connection with formula (I) above (i.e. ◯ is the skeleton of a polyol, n is a number from 3 to about 24 which represents the total number of hydroxy groups in the polyol, and p is a number $\geq 3$ and $\leq n$); and alkylene and Z are defined as in connection with formulas (V) and (VI) above. When a formula (V) starting material is used, the reaction is conducted in the presence of suitable coupling agent such as dicyclohexylcarbodiimide. Alternatively, a mixed anhydride or activated ester may be used. When a formula (VI) starting material is used, the reaction is typically conducted in the presence of a an acid scavenger such as triethylamine, in a halogenated hydrocarbon solvent, e.g. chloroform. The resultant polyester of formula (VII) is then converted to the desired quaternary ester intermediate of formula (III) wherein $R^+$ is structure (e) by contacting said polyester with excess reactant of the formula

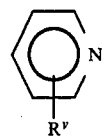 (VIII)

wherein $R^v$ is located in the 2-, 3- or 4-position and is H, —$CONH_2$ or —$COO(C_1$-$C_7$ alkyl), in a polar solvent such as nitromethane, dimethylformamide, acetonitrile, acetone, tetrahydrofuran of ethyl ether, followed by isolation by crystallization. The novel quaternary intermediate thus obtained wherein the anion is $Cl^-$, $Br^-$ or $I^-$ can then be subjected to anion exchange (via an anion exchange resin or the Kaminski et al method described hereinabove), when an intermediate is desired in which a different anion is present. Any of these novel quaternary intermediates can then reacted with sodium heparin as already described above to give the corresponding heparin salts of formula (I).

The final products and intermediates prepared by the synthetic procedures detailed above can be readily isolated and purified by usual separation means, for example, solvent extraction, dilution, recrystallization, column chromatography or preparative thin-layer chromatography.

The salts of formula (I) can be conveniently administered to warm-blooded animals via conventional oral, nasal or pulmonary (i.e. oral inhalation) administration, preferably by combining the active ingredient of formula (I) with a suitable non-toxic pharmaceutically acceptable inert oral, nasal or pulmonary carrier material, respectively. Such carrier materials are well-known to those skilled in the art of pharmaceutical formulations. For those not skilled in the art, reference is made to the text entitled REMINGTON'S PHARMACEUTICAL SCIENCES, fourteenth edition, 1970.

In a typical unit dosage form for oral administration, e.g. tablet or capsule, any one of the salts of formula (I) is combined, in an effective anticoagulant amount, with an oral non-toxic pharmaceutically acceptable inert carrier such as lactose, starch (pharmaceutical grade), dicalcium phosphate, calcium sulfate, kaolin, mannitol or powdered sugar. Additionally, when required or desired, suitable binders, lubricants, wetting agents, surface-active agents, disintegrating agents, coloring agents, flavoring agents and preservatives can also be included. Typical binders include starch, gelatin, sugars such as sucrose, molasses and lactose, natural and synthetic gums such as acacia, sodium alginate, extract of Irish Moss, carboxymethyl cellulose, methyl cellulose, polyvinylpyrrolidione, polyethylene glycol, ethyl cellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methyl cellulose, agar, bentonite, cellulose, wood products, alginic acid, guar gum, citrus pulp, carboxymethyl cellulose and sodium lauryl sulfate. The amount of active ingredient present in the composition will generally be from about 1 to about 70% by weight of the total composition.

Typical dosage forms and carriers for nasal and oral inhalation therapy will obviously depend on the exact nature of the particular dosage form desired, e.g. whether the ion pair is to be formulated into a nasal solution or suspension (typically for use as nose drops or nasal spray), a nasal ointment, cream or gel, or a formulation for oral inhalation. Preferred dosage forms for nasal administration are solutions, which contain a major amount of water in addition to the active ingredient. Minor amounts of other ingredients such as pH adjusters (e.g. a base such as NaOH), emulsifiers or dispersing agents, buffering agents, preservatives, wetting agents and jelling agents (e.g. methylcellulose) may also be present. Most preferably, the nasal composition is a sterile, isotonic, buffered aqueous solution or suspension in polyethylene glycol. The amount of formula (I) salt in the nasal composition will of course vary with the particular salt employed and the type of formulation selected. Generally speaking, the composition will contain 0.01 to 5% of a salt of formula (I), preferably 0.25 to 2.5%; in other words, each ml of solution or suspension will contain 0.1 to 50 mg, preferably 2.5 to 25 mg, of the formula (I) salt. In the case of oral inhalation therapy, compositions typically formulated for such route of administration may be used, a preferred dosage form being an oral inhalation aerosol containing the desired salt of formula (I) and fluorochlorohydrocarbons as propellants. Most preferably, the aerosol is provided with a metering mechanism to make accurate dosing possible. Each inhalation will typically deliver 0.1 to 50 mg, preferably 2.5 to 25 mg of the salt of formula (I).

The therapeutic dosage range for the salts of the instant invention will vary with the size and needs of the animal and the particular salt selected for administration. Generally speaking, the present "ion-pairs" can be orally administered in much smaller amounts by weight (e.g. less than one-half) and less frequently than would be necessary for orally administered sodium heparin itself. Administration as infrequently as once every 24 to 48 hours may be possible using selected ion pairs of this invention. When nasal or inhalation administration is used, dosages and frequency of administration may be similar to oral dosages and frequency of the instant ion pairs, although smaller, more frequent doses may be preferred for nasal or inhalation therapy. In any case, amounts to be administered by the selected route can be calculated on a unit basis, based on the potency of the heparin sodium used to prepare the instant salts, the new unit/mg potency being calculated based on the increase in molecular weight. The number of units given will approximate 2 to 10 times those currently used parenterally in the case of heparin sodium.

In order to further illustrate the present invention and the advantages thereof, specific examples are given below, it being understood that these examples are intended only as illustrative and in no way limitative. In the examples to follow, all melting points are uncorrected and were obtained by using electrothermal capillary melting point apparatus. Elemental analyses were performed at Atlantic Microlabs, Inc., Atlanta, Ga. In all cases where Anal. C, H, N is indicated, the elementary analysis of the material was found to be within ±0.4 of the calculated value.

EXAMPLE 1

To a suspension of 50 g (0.41 mol) of dry nicotinic acid in 135 ml of dry distilled pyridine were added 34 g of phosphorus oxychloride ($POCl_3$). The reaction mixture was stirred for one hour at 60° C., then 12.3 g (0.068 mol) of myo-inositol were added. The resultant mixture was maintained at 80° C., with stirring, for 3 hours, then was poured into 200 ml of ice cold water. The fine yellowish-white solid which separated was removed from the dark brown mother liquor by filtration, washed well with water and dried in a vacuum oven at 150° C. The solid was crystallized from a chloroform/ether solvent pair to afford 45 g (82% yield) of inositol hexanicotinate (1). The product melts at 258°–260° C. and can be represented by the structural formula

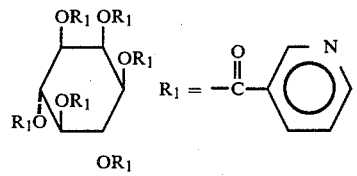

EXAMPLE 2

To a solution of 20 g (2.5 mmol) of inositol hexanicotinate (1) in 200 ml of dimethylformamide were added 11.2 g (0.08 mol) of methyl iodide. The mixture was heated at 50° C., under reflux, with stirring, for 48 hours. The fine yellow solid which separated was removed by filtration, washed with acetone and dried in a vacuum at 100° C. The product, obtained in 78% yield (3.2 g), was inositol hexa(1-methyl-3-pyridinium carboxylate)hexaiodide (2), melting at 250°–253° C. with decomposition. NMR ($D_2O$) δ 9.6–7.96 (ms, 24H, pyridinium protons), 6.7–6.6(m, 6H, inositol protons), 4.4 (s, 18H, 6 $CH_3-N^+$). Anal. ($C_{48}H_{48}I_6N_6O_{12}$) C, H, N. The product can be represented by the structural formula

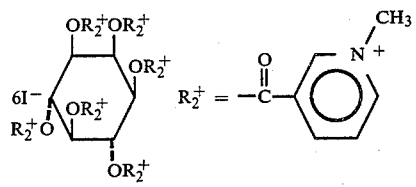

and can also be called hexa(N-methylnicotinoyloxy)cis-1,2,3,5-trans-4,6-cyclohexane hexaiodide.

EXAMPLE 3

To a solution of 2.0 g (2.5 mmol) of inositol hexanicotinate (1) in 200 ml of dimethylformamide were added 6.6 g (0.053 mol) of dimethylsulfate. The mixture was heated, with stirring, at 60° C. for forthy-eight hours. The sticky, yellowish residue which separated on addition of ether was repeatedly washed with acetone and then dried in a vacuum oven at 50° C. for twenty-four hours. There were thus obtained 2.5 g (64% yield) of inositol hexa(1-methyl-3-pyridinium carboxylate) hexa(methylsulfate) (3), as a yellow, highly hygroscopic solid. NMR ($D_2O$)δ9.60–8.03 ms, 24H, pyridinium protons), 6.6–6.5 (m, 6H inositol protons), 4.46 (s, 18H, 6

$CH_3$—$N^+$), 3.56 (s, 18H, 6 $CH_3$—$OSO_3$). Anal. ($C_{54}H_{66}N_6O_{36}S \cdot 6H_2O$) C, H, N. The product, which can also be named hexa(N-methylnicotinoyloxy)-cis-1,2,3,5-trans-4,6-cyclohexane hexa(methylsulfate), can be represented by the structural formula

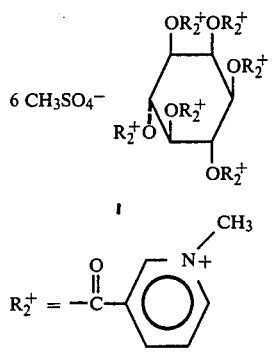

EXAMPLE 4

A solution of 1 mmol of the quaternary salt (2) or (3) in 10 ml of water was added, with stirring, to a solution of 1.14 g of heparin sodium (178.6 USP units/mg, 12% Na) in 10 ml of water. No precipitate was observed. On dilution with 100 ml of water, yellow oil droplets separated. The aqueous layer was removed by decantation and the residual oil was washed thoroughly several times with water. The well-drained oil was triturated with 50 ml of acetone. The oil solidified into a glistening yellow solid which was practically insoluble in organic solvents. The product weighed 1.6 g (84% of theoretical) and decomposed at 210° C. Use of the hexaiodide quaternary (2) gave a purer, easier to work with product than use of the hexa(methylsulfate) quaternary (3). Results of microanalysis for C, H, N and S for proposed formula $(C_{24}H_{34}Na_2N_2O_{35}S_5)_6{}^{5-}$. $(C_{48}H_{48}N_6O_{126}\cdot H_2O)_5{}^{6+}$: Calc. C, 39:32; H, 4:14; N, 5:01; S, 8:19. Found: C, 39:14; H, 4.72; N, 5.60; S, 7:64. The resultant heparin hexa(N-methylnicotinoyloxy)-cis-1,2,3,5-trans-4,6-cyclohexane salt (4) can also be represented by the structural formula

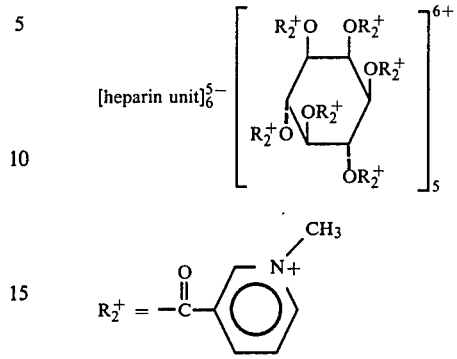

The anticoagulant activity of the product was calculated in relation to the sodium content of heparin sodium to be 107.6 units/mg.

EXAMPLE 5

A solution of 6 mmol of N,N-dimethyl-N-dodecyl-N-(β-hydroxyethyl)ammonium bromide in 10 ml of water was added, with stirring, to a solution of 1.14 g of heparin sodium (178.6 unit/mg, 12% Na) in 10 ml of water. A white percipitate was obtained. The mixture was centrifuged and the residue was washed thoroughly with water, then dried in a vacuum desiccator. The white mass was thus converted to a transparent, colorless plastic-like mass of heparin N,N-dimethyl-N-dodecyl-N-(β-hydroxyethyl)ammonium ion pair (5), which was soluble in methanol and ethanol, but insoluble in water, ether, chloroform or dichloromethane.

EXAMPLE 6

Substitution of an equivalent quantity of each of the starting materials listed below for the nicotinic acid employed in Example 1 and substantial repetition of the procedures there detailed affords, after suitable isolation, the indicated products of the formula

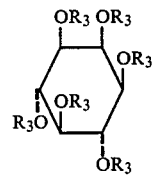

| STARTING MATERIAL | PRODUCT | |
|---|---|---|
| (picolinic acid) — N with COOH ortho | $R_3 = -\overset{O}{\underset{\|}{C}}-$ pyridyl (2-) | (6) |
| (isonicotinic acid) — N with COOH para | $R_3 = -\overset{O}{\underset{\|}{C}}-$ pyridyl (4-) | (7) |

-continued

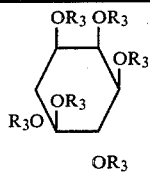

| STARTING MATERIAL | PRODUCT | |
|---|---|---|
| 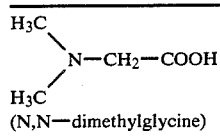 (N,N—dimethylglycine) | 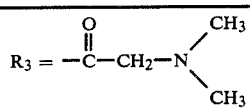 | (8) |
| 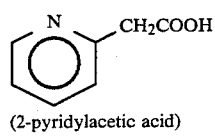 (2-pyridylacetic acid) | 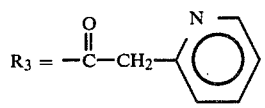 | (9) |
| 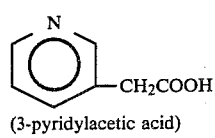 (3-pyridylacetic acid) | 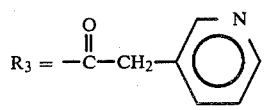 | (10) |
| 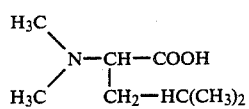 (N,N—dimethylleucine, prepared by reacting 2-bromo-4-methylpentanoic acid with dimethylamine) | 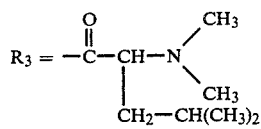 | (11) |
| 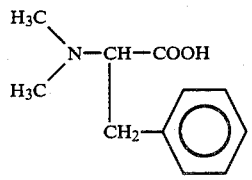 (N—N—dimethylphenylalanine, prepared by reacting 2-bromo-3-phenylpropionic acid with dimethylamine) | 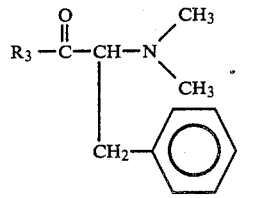 | (12) |
| 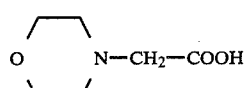 (the morpholino analogue of glycine, prepared by reacting bromoacetic acid with morpholine) | 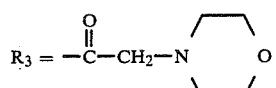 | (13) |
| 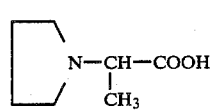 (the pyrrolidin-1-yl analogue of alanine, prepared by reacting 2-bromopropionic acid with pyrrolidine) | 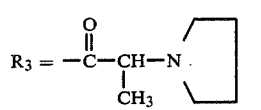 | (14) |
| 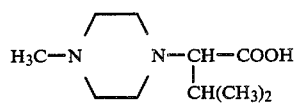 (the 4-methylpiperazine-1-yl analogue of valine, prepared by reacting 2-bromo-3-methylbutanoic acid with | 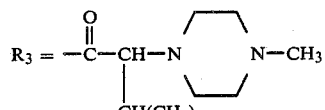 | (15) |

-continued

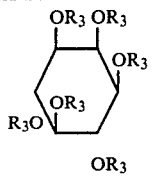

| STARTING MATERIAL | PRODUCT | |
|---|---|---|
| N—methylpiperazine) | | |
| H₅C₂\N—CH₂—COOH /H₅C₂ (N,N—dimethylglycine, prepared by reacting bromoacetic acid with diethylamine) | $R_3 = -\overset{O}{\underset{\|}{C}}-CH_2-N\begin{smallmatrix}C_2H_5\\C_2H_5\end{smallmatrix}$ | (16) |

EXAMPLE 7

Substitution of an equivalent quantity of each of the starting materials listed below for the inositol employed in Example 1 and substantial repetition of the procedures there detailed affords, after appropriate isolation, the indicated products:

| STARTING MATERIAL | PRODUCT | | |
|---|---|---|---|
| (α-D-glucose) | (glucose with OR₃) | $R_3 = -\overset{O}{\underset{\|}{C}}-\text{pyridyl}$ | (17) |
| erythritol (H₂COH-HCOH-HCOH-H₂COH) | H₂COR₃-HCOR₃-HCOR₃-H₂COR₃ | $R_3 = -\overset{O}{\underset{\|}{C}}-\text{pyridyl}$ | (18) |
| (α-D-ribofuranose) | (ribofuranose with OR₃) | $R_3 = -\overset{O}{\underset{\|}{C}}-\text{pyridyl}$ | (19) |
| α-D-galactose | (galactose with OR₃) | $R_3 = -\overset{O}{\underset{\|}{C}}-\text{pyridyl}$ | (20) |
| lactose | (lactose with OR₃) | $R_3 = -\overset{O}{\underset{\|}{C}}-\text{pyridyl}$ | (21) |

| STARTING MATERIAL | PRODUCT |
|---|---|

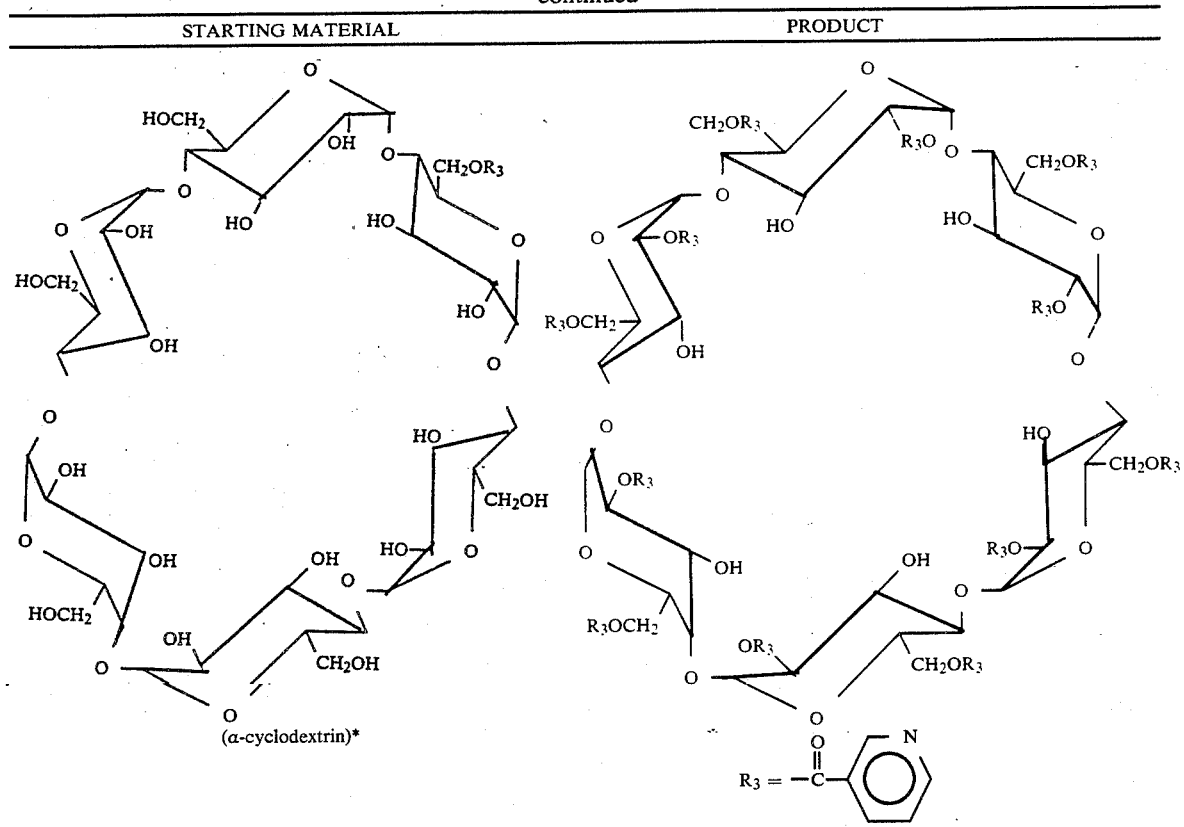

(α-cyclodextrin)*

*When using this polyol, the molar ration of nicotinic acid to polyol is at least 12:1.

EXAMPLE 8

Substitution of an equivalent quantity of each of the starting materials listed in Column A below for the inositol used in Example 1 and substitution of an equivalent quantity of each of the starting materials listed in Column B below for the nicotinic acid used in Example 1 affords, by the procedures of that Example, the following products:

| COLUMN A | COLUMN B | PRODUCT | |
|---|---|---|---|
| 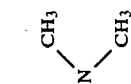<br>(α-D-glucose) | 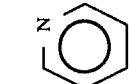<br>(picolinic acid) |  | (23) |
| <br>(α-D-glucose) | <br>(N,N—dimethylglycine) |  | (24) |
| <br>(α-D-glucose) | <br>(3-pyridylacetic acid) | | (25) |
| (α-D-ribofuranose) | | | (26) |

-continued

| | COLUMN A | COLUMN B | PRODUCT | |
|---|---|---|---|---|
| (27) | (α-D-galactose) | (N,N-dimethylphenylalanine) | $R_3 = -\overset{O}{\underset{\|}{C}}-CH-N(CH_3)_2$ with $CH_2$-phenyl | |
| (28) | (α-D-ribofuranose) | (the pyrrolidin-1-yl analogue of valine) | $R_3 = -\overset{O}{\underset{\|}{C}}-CH-N\text{(pyrrolidine)}$ with $CH_3$ | |
| (29) | (α-D-galactose) | (the 4-methylpiperazin-1-yl analogue of valine) | $R_3 = -\overset{O}{\underset{\|}{C}}-CH-N\text{(4-methylpiperazine)}$ with $CH(CH_3)_2$ | |
| (30) | (lactose) | (N,N-diethylglycine) | $R_3 = -\overset{O}{\underset{\|}{C}}-CH_2-N(C_2H_5)_2$ | |

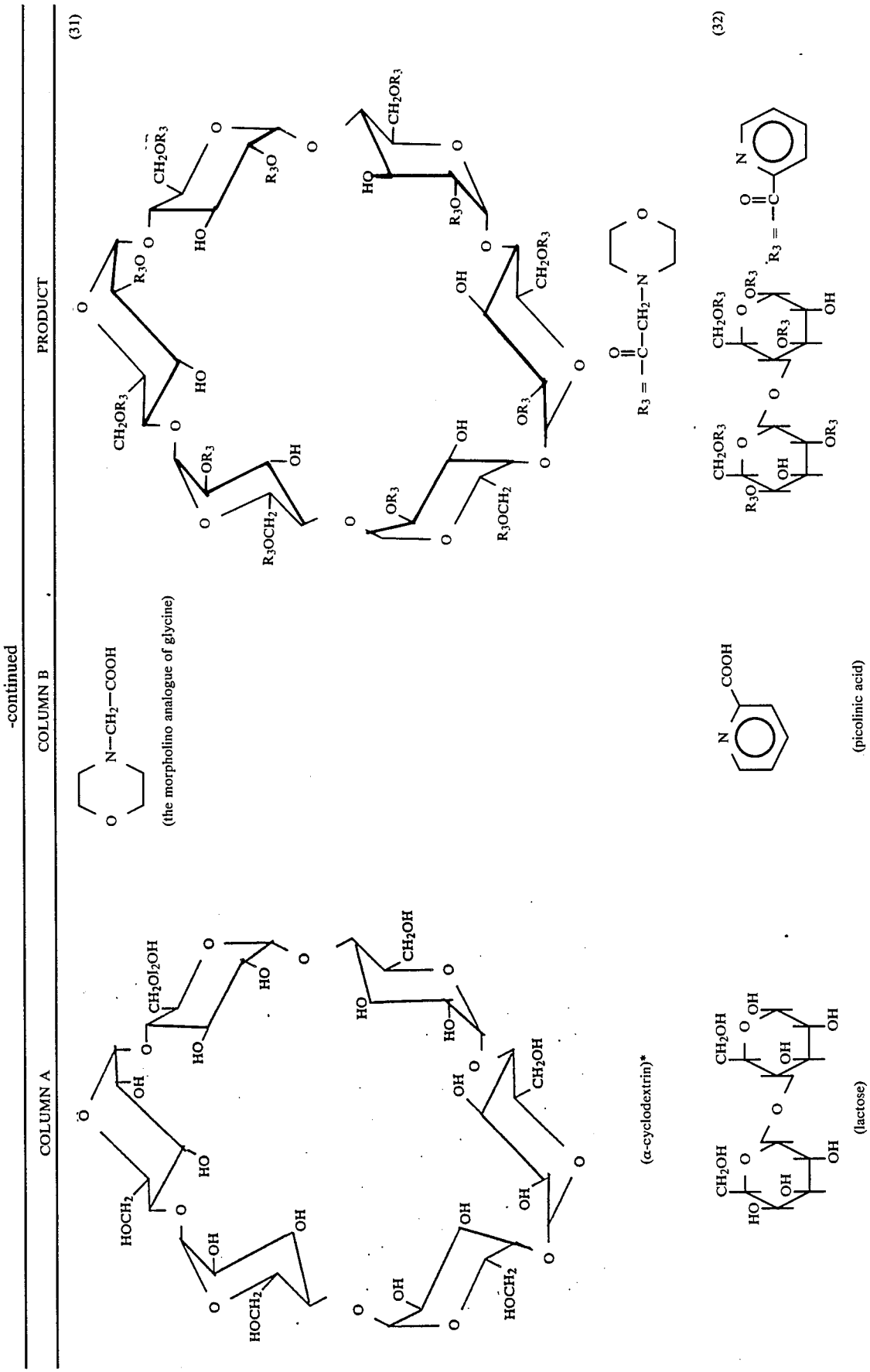

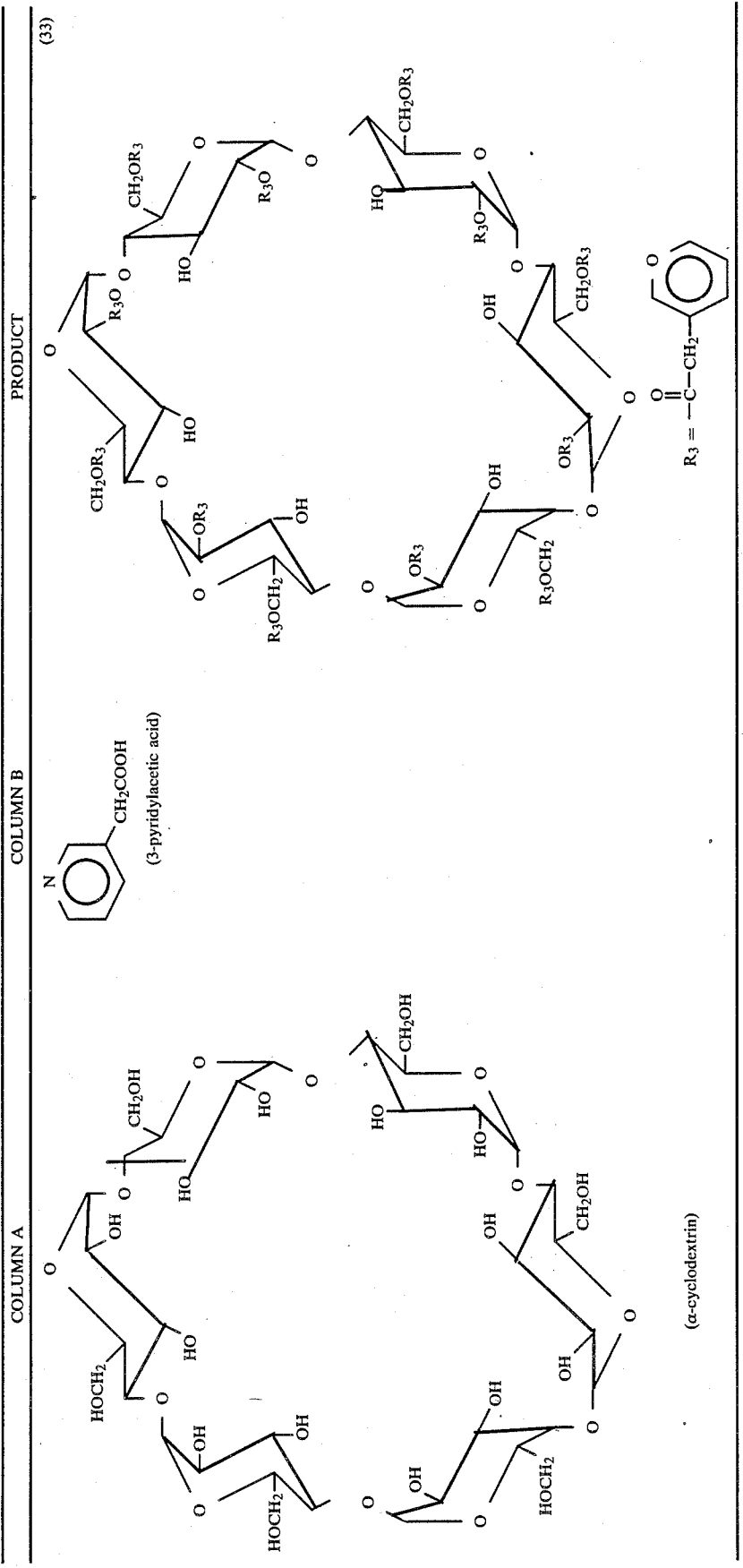
*When using this polyol, the molar ratio of Column B starting material to polyol is at least 12:1.

EXAMPLE 9

Quaternization of each of the products of Examples 6, 7 and 8 according to the general procedure of Example 2 affords, after appropriate isolation, the following products:

| STARTING MATERIAL | PRODUCT | |
|---|---|---|
| Example 6, Compound (6) | 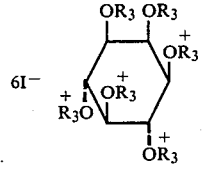 | 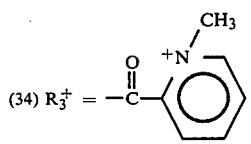 (34) $R_3^+ = $ |
| Example 6, Compound (7) | 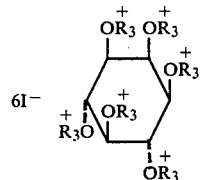 | 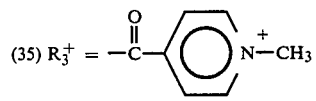 (35) $R_3^+ = $ |
| Example 6, Compound (8) | 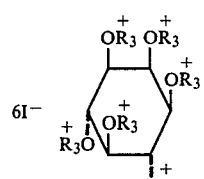 | (36) $R_3^+ = -\overset{\overset{O}{\|}}{C}-CH_2-\overset{+}{N}\begin{subarray}{l}CH_3\\CH_3\\CH_3\end{subarray}$ |
| Example 6, Compound (9) | 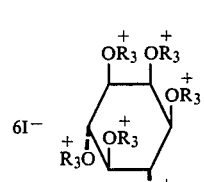 | 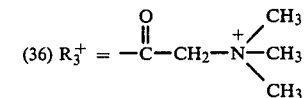 (37) $R_3^+ = $ |
| Example 6, Compound (10) | 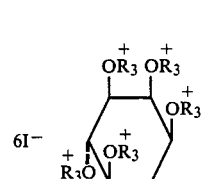 | 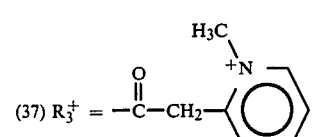 (38) $R_3^+ = $ |
| Example 6, Compound (11) | 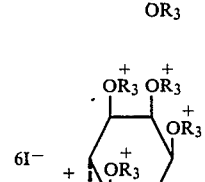 | (39) $R_3^+ = -\overset{\overset{O}{\|}}{C}-\underset{\underset{CH_2-CH(CH_3)_2}{\|}}{CH}-\overset{+}{N}(CH_3)_3$ |
| Example 6, Compound (12) | 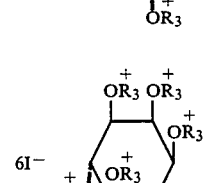 | (40) $R_3^+ = -\overset{\overset{O}{\|}}{C}-\underset{\underset{CH_2-\text{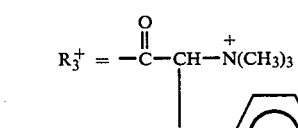}}{\|}}{CH}-\overset{+}{N}(CH_3)_3$ |

| STARTING MATERIAL | PRODUCT | |
|---|---|---|
| Example 6, Compound (13) | 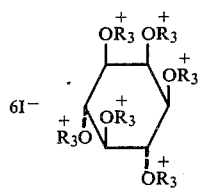 | 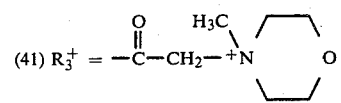 |
| Example 6, Compound (14) | 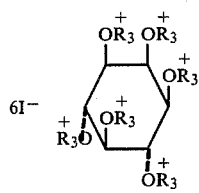 | 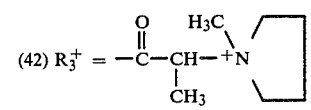 |
| Example 6, Compound (15) | 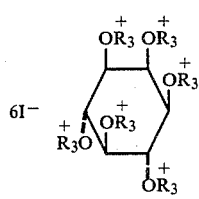 | 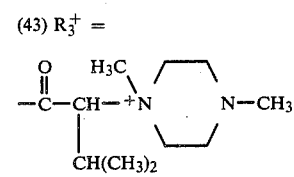<br>and<br>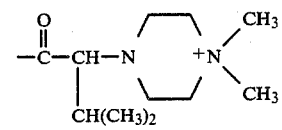 |
| Example 6, Compound (16) | 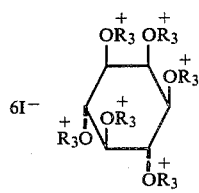 | 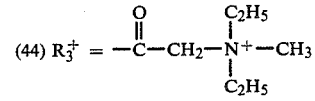 |
| Example 7, Compound (17) | 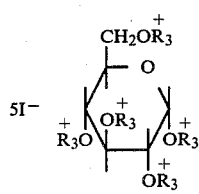 | 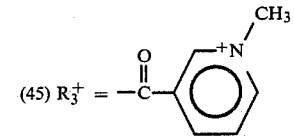 |
| Example 7, Compound (18) | 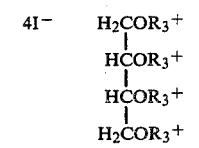 | 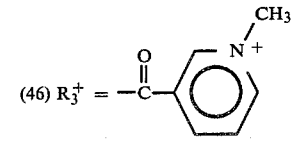 |
| Example 7, Compound (19) | 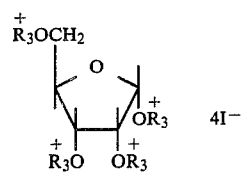 | 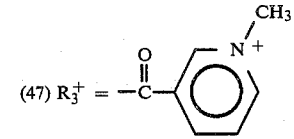 |

-continued

| STARTING MATERIAL | PRODUCT | |
|---|---|---|
| Example 7, Compound (20) | 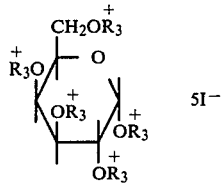 | (48) $R_3^+ = \underset{O}{\overset{\parallel}{-C}}-\underset{}{\overset{CH_3}{\underset{|}{N^+}}}\!\!\!\!\bigcirc$ |
| Example 7, Compound (21) | 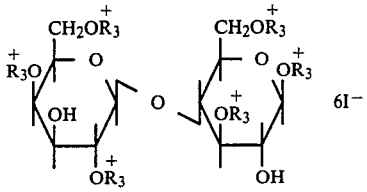 | (49) $R_3^+ = \underset{O}{\overset{\parallel}{-C}}-\underset{}{\overset{CH_3}{\underset{|}{N^+}}}\!\!\!\!\bigcirc$ |
| Example 7, Compound (22)* | 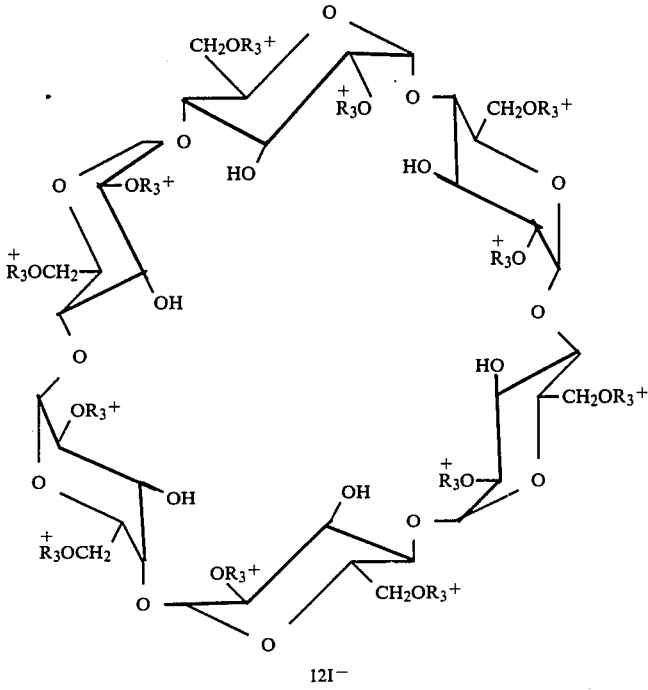 | (50) $R_3^+ = \underset{O}{\overset{\parallel}{-C}}-\underset{}{\overset{CH_3}{\underset{|}{N^+}}}\!\!\!\!\bigcirc$ |
| Example 8, Compound (23) | 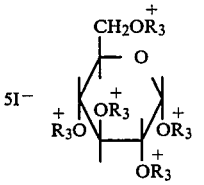 | (51) $R_3^+ = \underset{O}{\overset{\parallel}{-C}}-\underset{}{\overset{CH_3}{\underset{|}{N^+}}}\!\!\!\!\bigcirc$ |
| Example 8, Compound (24) | 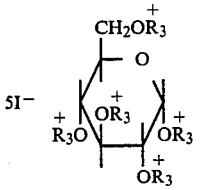 | (52) $R_3^+ = -\overset{O}{\overset{\parallel}{C}}-CH_2-\overset{+}{N}(CH_3)_3$ |

-continued

| STARTING MATERIAL | PRODUCT | |
|---|---|---|
| Example 8, Compound (25) | [pyranose ring with CH₂OR₃⁺, OR₃⁺, OR₃⁺, R₃O⁺, 5I⁻] | (53) $R_3^+$ = $-\overset{O}{\underset{\|}{C}}-CH_2-\underset{}{\overset{+}{N}}$(3-methylpyridinium with N-CH₃) |
| Example 8, Compound (26) | [furanose ring with R₃OCH₂⁺, OR₃⁺, OR₃⁺, 4I⁻] | (54) $-\overset{O}{\underset{\|}{C}}-$(4-pyridinium)-N⁺-CH₃ |
| Example 8, Compound (27) | [pyranose ring with CH₂OR₃⁺, OR₃⁺, OR₃⁺, R₃O⁺, 5I⁻] | $R_3^+$ = $-\overset{O}{\underset{\|}{C}}-CH-\overset{+}{N}(CH_3)_3$<br>                $\|$<br>                $CH_2$<br>                $\|$<br>                (phenyl) (55) |
| Example 8, Compound (28) | [furanose ring with R₃OCH₂⁺, OR₃⁺, OR₃⁺, R₃O⁺, 4I⁻] | (56) $R_3^+$ = $-\overset{O}{\underset{\|}{C}}-CH-\overset{H_3C}{\underset{CH_3}{\overset{\|}{N^+}}}$(pyrrolidine ring) |
| Example 8, Compound (29) | [pyranose ring with CH₂OR₃⁺, OR₃⁺, OR₃⁺, R₃O⁺, 5I⁻] | (57) $R_3^+$ =<br>$-\overset{O}{\underset{\|}{C}}-CH-\overset{H_3C}{\underset{CH(CH_3)_2}{\overset{\|}{N^+}}}$(piperazine)$N-CH_3$<br><br>and<br><br>$-\overset{O}{\underset{\|}{C}}-CH-N$(piperazine)$\overset{+}{N}\overset{CH_3}{\underset{CH_3}{}}$<br>       $\|$<br>       $CH(CH_3)_2$ |
| Example 8, Compound (30) | [disaccharide with CH₂OR₃⁺, R₃O⁺, OH, OR₃⁺, O-link, CH₂OR₃⁺, OR₃⁺, OR₃⁺, OH, 6I⁻] | (58) $R_3^+$ = $-\overset{O}{\underset{\|}{C}}-CH_2-\overset{+}{\underset{CH_3}{N}}(C_2H_5)_2$ |

-continued
| STARTING MATERIAL | PRODUCT | |
|---|---|---|
| Example 8, Compound (31)* | 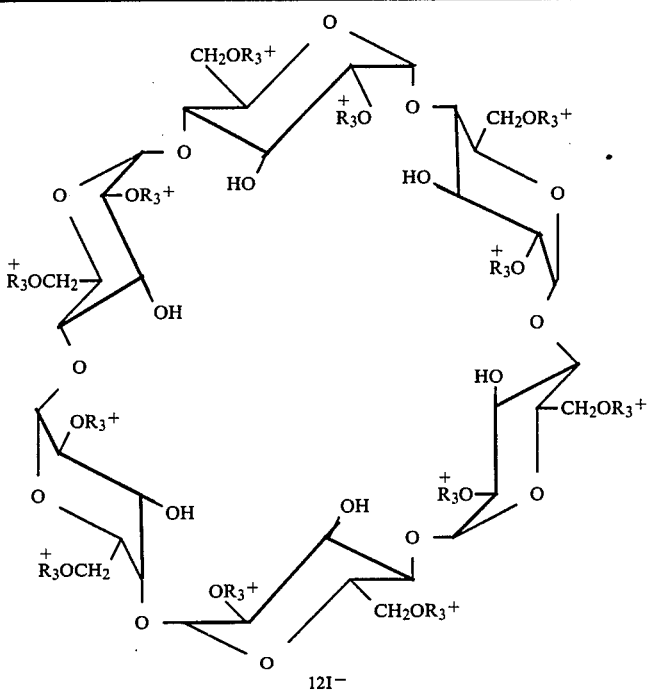 | 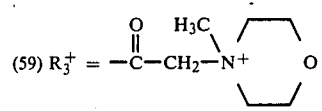(59) $R_3^+ = -\overset{O}{\underset{\|}{C}}-CH_2-\overset{+}{N}\begin{pmatrix}H_3C\\\ \end{pmatrix}O$ |
| Example 8, Compound (32) | 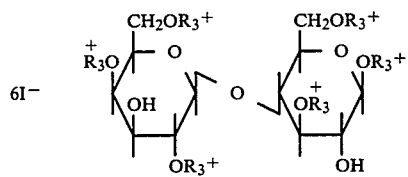 | 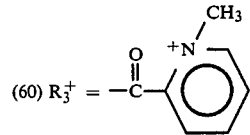(60) $R_3^+ =$ |
| Example 8, Compound (33)* | 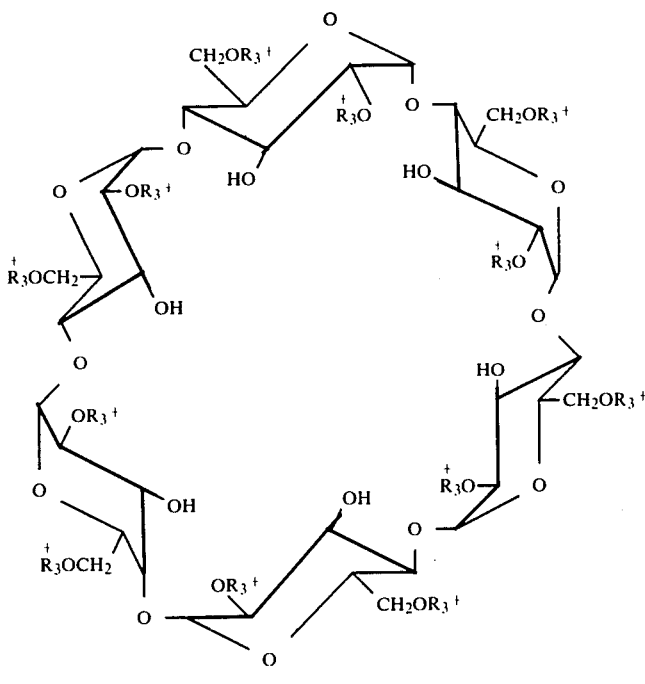 | (61) 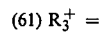$R_3^+ =$ 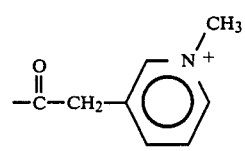 |
*When using this polyester as the starting material, an even greater excess of methyl iodide is preferably used than is employed in Example 2.

EXAMPLE 10

The general procedure of Example 4 is repeated, using an equivalent quantity of each of the quaternary salts prepared in Example 9 in place of the quaternary salt (2) or (3) used in Example 4 and varying reaction conditions appropriately when ion pairs of heparin$^{6-}$ or heparin$^{7-}$ are desired. After suitable isolation, the following heparin salts of the invention are obtained:

| PRODUCT |
|---|

STARTING MATERIAL Example 9, Compound (34)

[heparin unit]$_6^{5-}$ $R_3^+ = $ —C(=O)—(pyridinium ring with N$^+$—CH$_3$)

$\left[ \text{sugar unit with } OR_3^+ \text{ groups and } R_3^+O \right]_5^{6+}$      (62)

STARTING MATERIAL Example 9, Compound (35)

[heparin unit]$_6^{7-}$ $R_3^+ = $ —C(=O)—(phenyl)—N$^+$—CH$_3$ $\left[ \text{sugar unit with } OR_3^+ \text{ groups} \right]_7^{6+}$      (63)

STARTING MATERIAL Example 9, Compound (36)

[heparin unit]$^{6-}$ $R_3^+ = $ —C(=O)—CH$_2$—N$^+$(CH$_3$)$_3$ $\left[ \text{sugar unit with } OR_3^+ \text{ groups} \right]^{6+}$      (64)

STARTING MATERIAL Example 9, Compound (37)

[heparin unit]$_6^{5-}$ $R_3^+ = $ —C(=O)—CH$_2$—(pyridinium with H$_3$C—N$^+$)

$\left[ \text{sugar unit with } OR_3^+ \text{ groups} \right]_5^{6+}$      (65)

STARTING MATERIAL Example 9, Compound (38)

[heparin unit]$_6^{5-}$ $R_3^+ = $ —C(=O)—CH$_2$—(phenyl)—N$^+$—CH$_3$ $\left[ \text{sugar unit with } OR_3^+ \text{ groups} \right]_5^{6+}$      (66)

STARTING MATERIAL Example 9, Compound (39)

| PRODUCT | |
|---|---|
| [heparin unit]$_6^{5-}$ 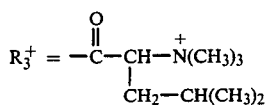 $R_3^+ = -\overset{O}{\underset{\|}{C}}-\underset{\underset{CH_2-CH(CH_3)_2}{\|}}{CH}-\overset{+}{N}(CH_3)_3$ | 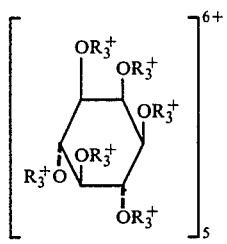 (67) |
| STARTING MATERIAL Example 9, Compound (40) | |
| [heparin unit]$_6^{5-}$ 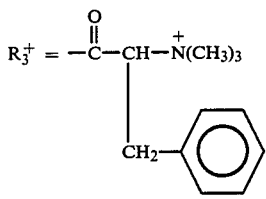 $R_3^+ = -\overset{O}{\underset{\|}{C}}-\underset{\underset{CH_2-\phi}{\|}}{CH}-\overset{+}{N}(CH_3)_3$ | 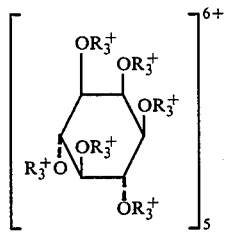 (68) |
| STARTING MATERIAL Example 9, Compound (41) | |
| [heparin unit]$_6^{5-}$ 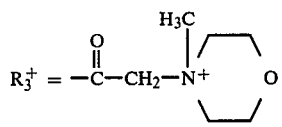 | 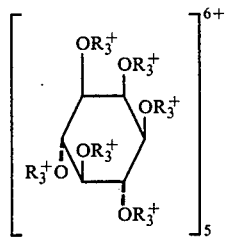 (69) |
| STARTING MATERIAL Example 9, Compound (42) | |
| [heparin unit]$_6^{5-}$ 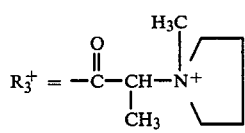 | 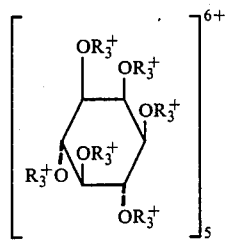 (70) |
| STARTING MATERIAL Example 9, Compound (43) | |
| [heparin unit]$_6^{5-}$ 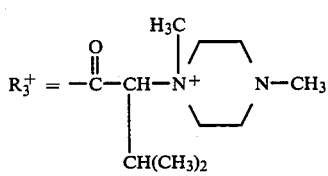 and 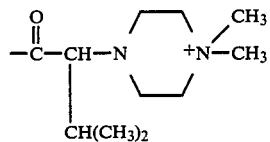 | 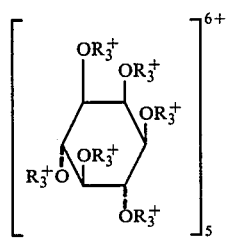 (71) |
| STARTING MATERIAL Example 9, Compound (44) | |

-continued
PRODUCT
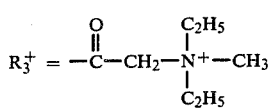
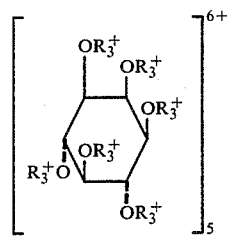 (71)
STARTING MATERIAL Example 9, Compound (45)
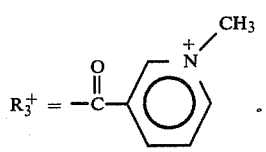
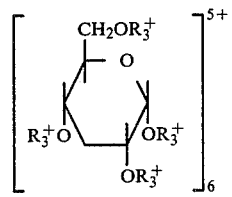 (73)
STARTING MATERIAL Example 9, Compound (46)
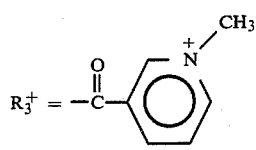
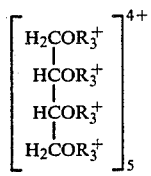 (74)
STARTING MATERIAL Example 9, Compound (47)
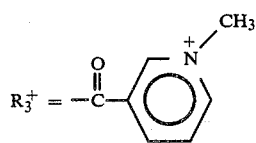
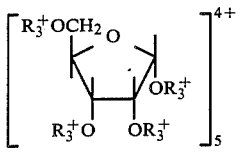 (75)
STARTING MATERIAL Example 9, Compound (48)
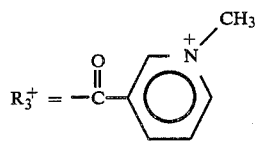
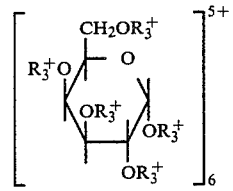 (76)
STARTING MATERIAL Example 9, Compound (49)
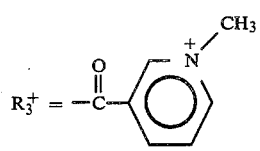
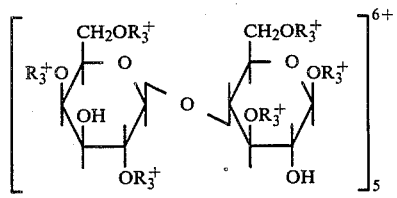 (77)
STARTING MATERIAL Example 9, Compound (50)

| PRODUCT | |
|---|---|
| [heparin unit]$_{12}^{5-}$ 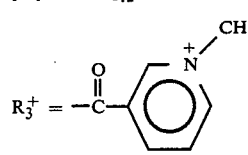 | 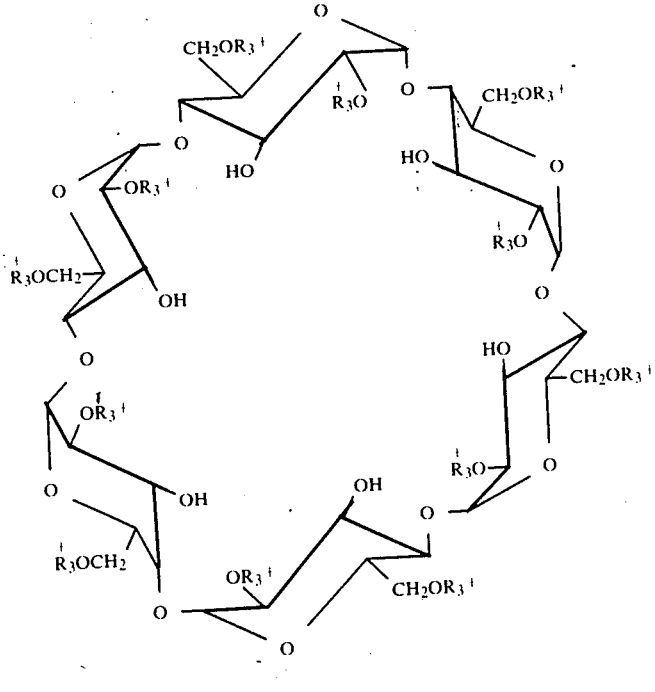 (78) |
| STARTING MATERIAL Example 9, Compound (51) | |
| [heparin unit]$_5^{5-}$ 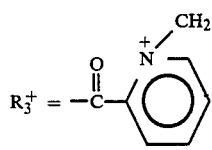 | 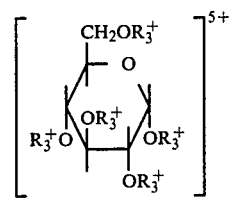 (79) |
| STARTING MATERIAL Example 9, Compound (52) | |
| [heparin unit]$_5^{6-}$ 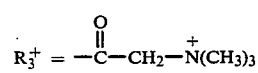 | 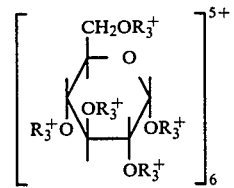 (80) |
| STARTING MATERIAL Example 9, Compound (53) | |
| [heparin unit]$_5^{7-}$ 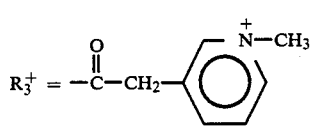 | 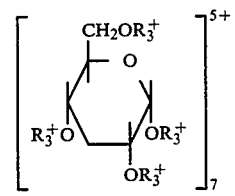 (81) |
| STARTING MATERIAL Example 9, Compound (54) | |
| [heparin unit]$_4^{5-}$ 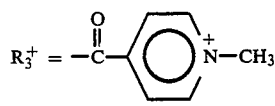 | 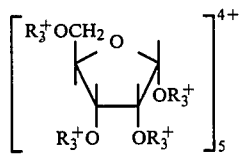 (82) |
| STARTING MATERIAL Example 9, Compound (55) | |

-continued

PRODUCT

(83) [heparin unit]$^{5-}$ $$R_3^+ = -\overset{O}{\underset{}{C}}-CH-\overset{+}{N}(CH_3)_3$$
$$\qquad\qquad |$$
$$\qquad\qquad CH_2-C_6H_5$$

$$\left[ \begin{array}{c} CH_2OR_3^+ \\ R_3^+O \quad O \\ OR_3^+ \quad OR_3^+ \\ OR_3^+ \end{array} \right]^{5+}$$

STARTING MATERIAL Example 9, Compound (56)

(84) [heparin unit]$^{5-}_4$ $$R_3^+ = -\overset{O}{\underset{}{C}}-CH-\overset{H_3C}{\underset{CH_3}{\overset{|}{N^+}}}\underset{}{\bigcirc}$$

$$\left[ \begin{array}{c} R_3^+OCH_2 \quad O \\ OR_3^+ \\ R_3^+O \quad OR_3^+ \end{array} \right]^{4+}_5$$

STARTING MATERIAL Example 9, Compound (57)

(85) [heparin unit]$^{6-}_5$ $$R_3^+ = -\overset{O}{\underset{}{C}}-CH-\overset{H_3C}{\underset{CH(CH_3)_2}{\overset{|}{N^+}}}\underset{}{\bigcirc}N-CH_3$$

and $$-\overset{O}{\underset{}{C}}-CH-N\underset{}{\bigcirc}\overset{CH_3}{\underset{CH_3}{\overset{|}{^+N}}}$$

$$\left[ \begin{array}{c} CH_2OR_3^+ \\ R_3^+O \quad O \\ OR_3^+ \quad OR_3^+ \\ OR_3^+ \end{array} \right]^{5+}_6$$

STARTING MATERIAL Example 9, Compound (58)

(86) [heparin unit]$^{5-}_6$ $$R_3^+ = -\overset{O}{\underset{}{C}}-CH_2-\overset{+}{N}(C_2H_5)_2$$
$$\qquad\qquad\qquad |$$
$$\qquad\qquad\qquad CH_3$$

$$\left[ \begin{array}{cc} CH_2OR_3^+ & CH_2OR_3^+ \\ R_3^+O \quad O & O \quad OR_3^+ \\ OH & OR_3^+ \\ OR_3^+ & OH \end{array} \right]^{6+}_5$$

STARTING MATERIAL Example 9, Compound (59)

(87) [heparin]$^{5-}_{12}$ $$R_3^+ = -\overset{O}{\underset{}{C}}-CH_2-\overset{H_3C}{\underset{}{\overset{|}{N^+}}}\underset{}{\bigcirc}O$$

$$\left[ \begin{array}{c} \text{complex polysaccharide structure with } CH_2OR_3, R_3O, OR_3 \text{ groups} \end{array} \right]^{12+}$$

PRODUCT

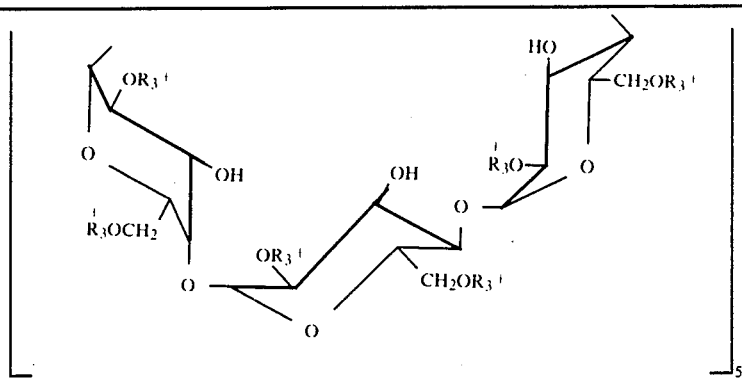

STARTING MATERIAL Example 9, Compound (60)

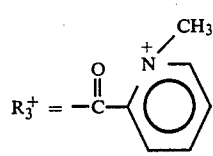

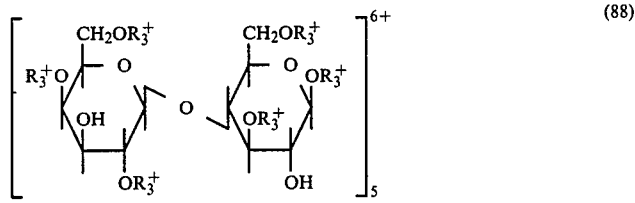

(88)

STARTING MATERIAL Example 9, Compound (61)

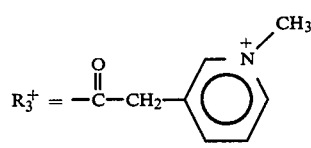

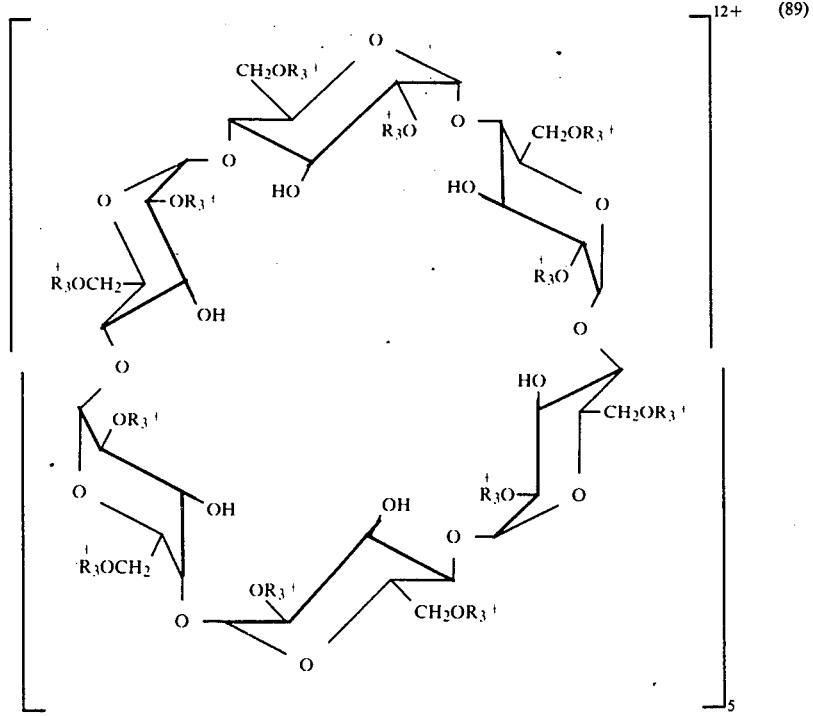

(89)

EXAMPLE 11

1.0 Mol of erythritol and 5.0 mol of Br—CH$_2$CH$_2$COCl are combined in chloroform (25 ml chloroform per 1.0 g erythritol) and 5.0 mol of triethylamine are added. The mixture is heated to the boiling point of chloroform and maintained at that temperature for approximately 4 hours, then washed successively with water, aqueous sodium bicarbonate solution and water and evaporated. The residue, which is the fully bromoacetylated intermediate of the formula

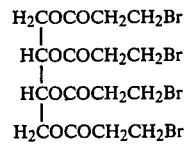

is then dissolved in dimethylformamide (25 ml dimethylformamide per 1.0 g of above intermediate) and excess nicotinamide (8.0 mol per 1.0 mol of above intermediate) is added. The mixture is warmed to 60°–70° C. and maintained at that temperature for about 24 hours. Acetonitrile is added to complete precipitation and the precipitate is removed by filtration and dried. The resultant novel intermediate of the formula

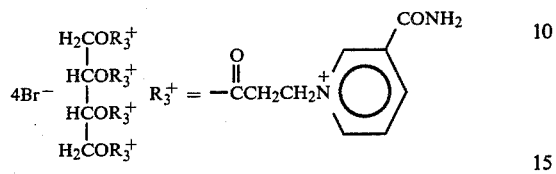

can then be reacted with heparin sodium according to the procedure of Example 4 to afford the following heparin salt of the invention:

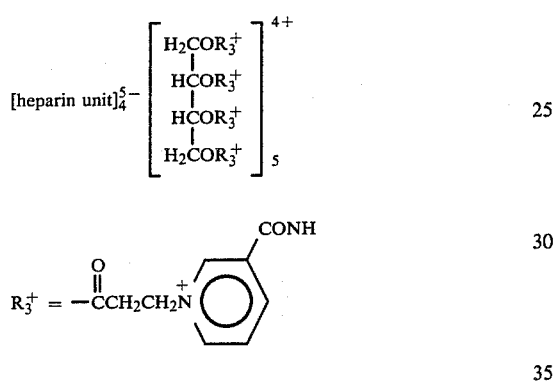

Substantial repetition of the foregoing general procedure utilizing an equivalent quantity of α-D-ribofuranose in place of the erythritol affords, in the first step, the bromoacetylated intermediate of the formula

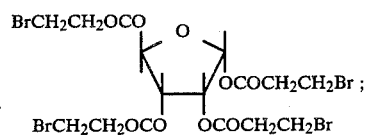

in the second step, the novel quaternary intermediate of the formula

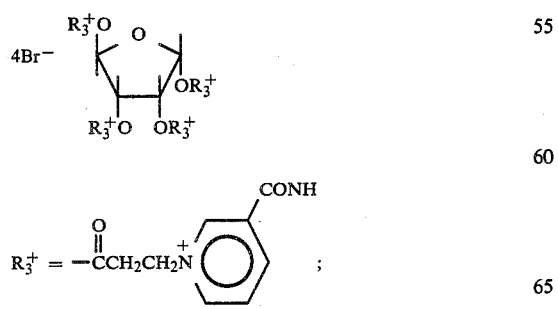

and, in the third step, the following heparin salt of the invention:

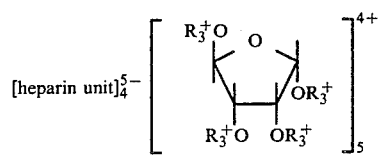

EXAMPLE 12

1.0 Mol of inositol, 6.6 mol of pyridinium acetic acid bromide (prepared by reacting pyridine with bromoacetic acid) and 6 mol of dicyclohexylcarbodiimide are combined in pyridine (30 ml per 1.0 g inositol). The mixture is stirred for approximately 4 to 6 hours at room temperature. After appropriate isolation and purification, the following novel quaternary intermediate is obtained:

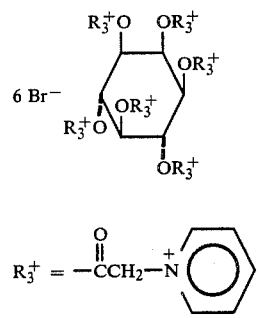

Reaction of that novel intermediate with heparin sodium according to the procedure of Example 4 affords the following heparin salt of the invention:

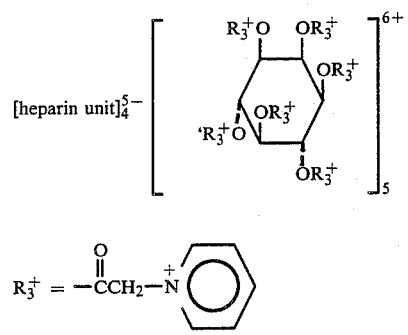

EXAMPLE 13

Substitution of equivalent quantities of the starting materials listed below for the inositol and pyridinium acetic acid bromide used in Example 12 and repetition of the general procedure described in the first paragraph of that example affords the indicated products:

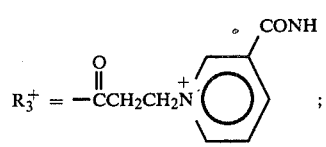

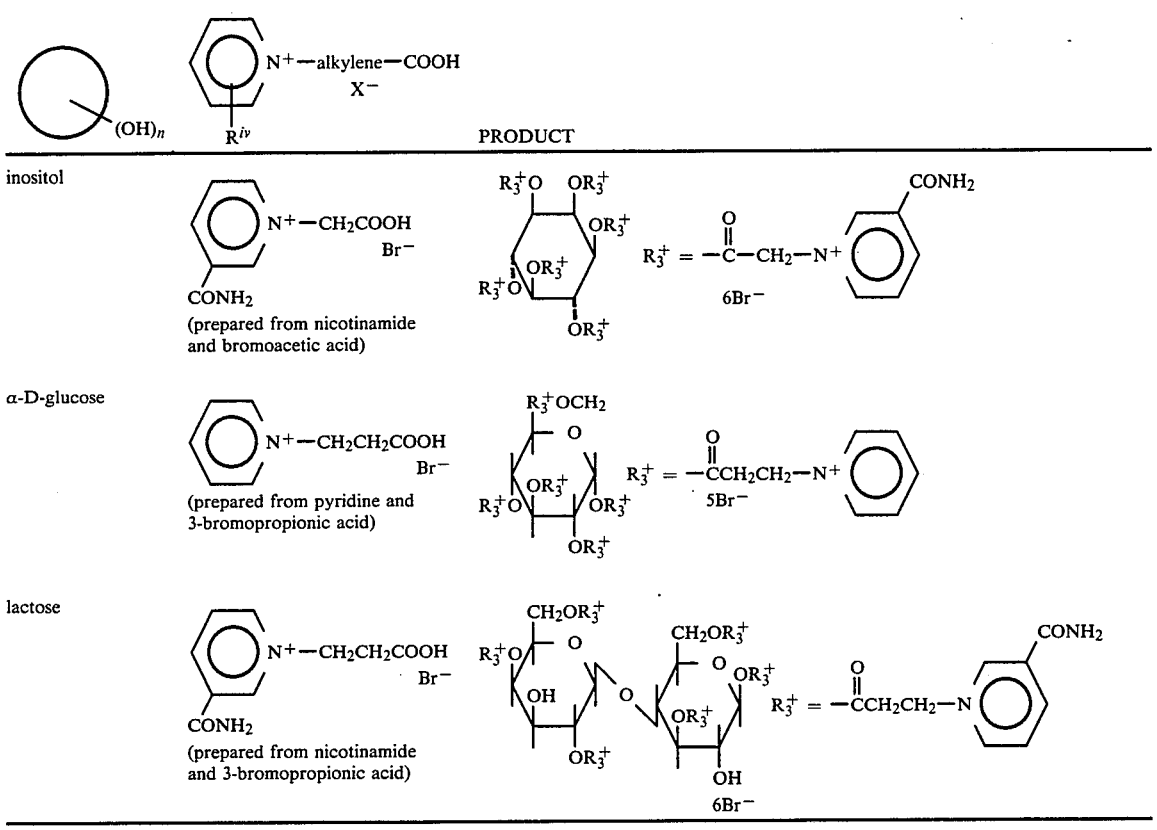
EXAMPLE 14
Reaction of each of the products of Example 13 with heparin sodium according to the procedure of Example 4 affords the following heparin salts of the invention:
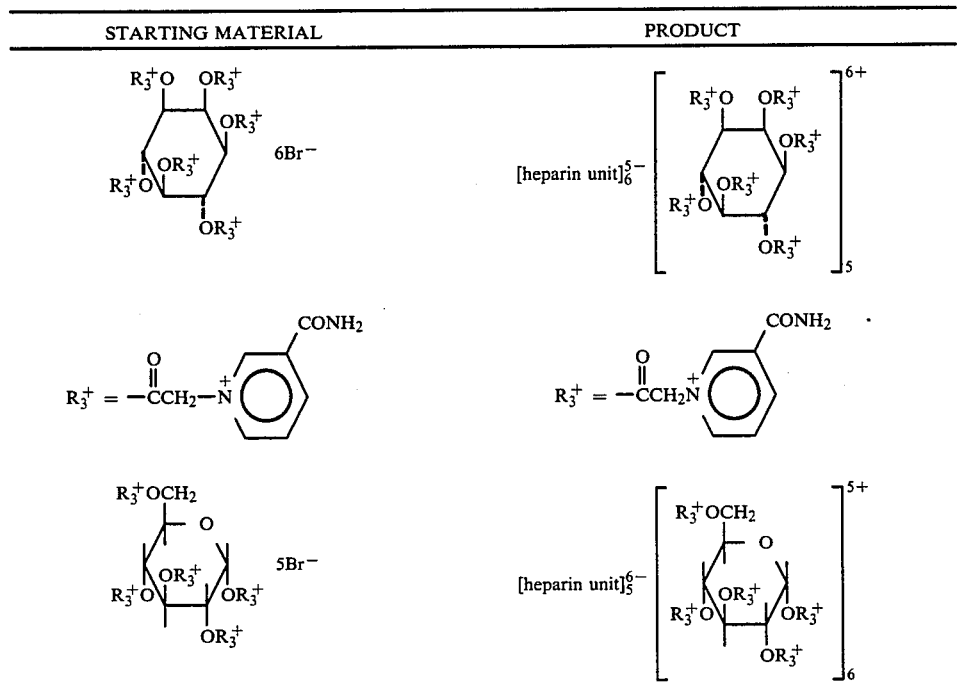

| STARTING MATERIAL | PRODUCT |
|---|---|

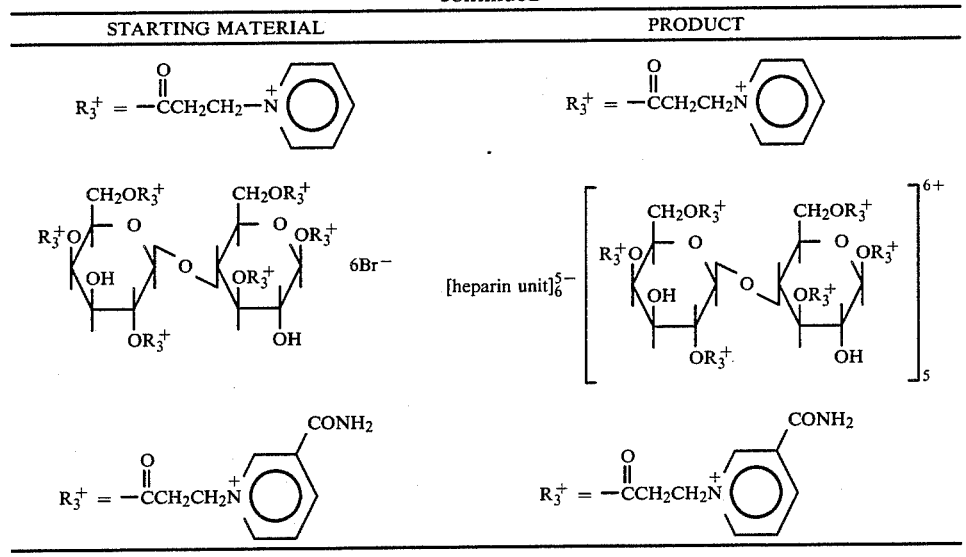

EXAMPLE 15

Stability Studies

A solution of (3) in $D_2O$ was maintained at room temperature in a NMR sample tube and an NMR run was taken daily. The only observed difference was a broadening of the multiplet at $\delta$ 6.6–6.5 corresponding to the protons of the inositol ring which started three days after preparing the solution for study. The broadening increased and the absorption shifted upfield until it lost its characteristic shape (within 12 days).

EXAMPLE 16

Pharmacological Testing

Determination of Clotting Time

Blood was withdrawn from the treated or control animals, rat or rabbit, by cardiac puncture. Each blood sample was divided into three 1.5 ml polypropylene microcentrifuge tubes. The tubes were capped and the tube containing the first blood withdrawn was inverted once every 30 sec until the blood clotted. At this time, the next tube was inverted in the same way followed by the third tube, which contained the last blood withdrawn. The clotting time taken was the time the blood in the third tube coagulated.

Testing of Anticoagulant Activity by Oral Administration to Rats

Male Sprague-Dawley rats with an average weight of 450 g were used. The rats were anesthetized with ether and either the test drug or heparin sodium, with a dose of 9000 USP unit/rat, was given orally through a stomach tube as a suspension in 1 ml polyethylene glycol 400. A group of rats were treated in the same way with 1 ml polyethylene glycol 400 only and was used as control. At selected time intervals, a sample of blood was withdrawn by cardiac puncture and the clotting time was determined as described previously.

Testing of Anticoagulant Activity of Jejunal Administration to Rats and Rabbits

Male Sprague-Dawley rats with an average weight of 450 g and New Zealand white rabbits of average weight 3.0 kg were used for this mode of administration. The animals were fasted for twenty-four hours before the test. The abdomen of the anesthetized animal was entered and the jejunum identified. The finely powdered ion pair compound or heparin sodium, adjusted to contain a dose of 20,000 USP unit/kg, was suspended in polyethylene glycol 400 and injected directly into the jejunum. Blood samples were taken by cardiac puncture at selected time intervals after administration and the clotting time determined as described previously. With rats, no samples could be taken at more than four hours after administration because of the death of rats from internal bleeding.

Results

The in vitro anticoagulant activity of the heparin complexes (4) and (5) was tested. Their in vitro activity was found to be compared to their corresponding content of heparin. Their in vivo anticoagulant activity was tested compared to heparin sodium on rats using oral, rectal and jejunal administration and on rabbits using jejunal administration. The compounds and heparin sodium were each administered as a suspension in polyethylene glycol 400. [Compound (4) changed into a sticky semisolid when it came in contact with water.] Blood samples were taken by heart puncture and the clotting time was determined using the method described above. With rectal administration to rats, no activity was shown, whether for the complexes or for the heparin sodium. With oral administration to rats (FIG. 11), compound (5) showed no activity while compound (4), a representative heparin salt of this invention, showed higher activity than heparin, almost twice, after twenty-four hours. In the case of jejunal administration to rats (FIG. 2), compound (5) showed no activity while compound (4), the representative heparin salt of this invention, showed a larger AUC (area under the curve) within the four hours of the experiment. No data could be collected for longer time periods for administration, since the rats died from internal hemorrhage due to the operation. With jejunal administration to rabbits (FIG. 3), it is shown that, although compound (4) has slower onset of action than heparin sodium, it is more active and has a much longer duration of action. The clotting time does not return back to the normal value except after about 90 hours from administration. One rabbit was sacrificed and dissected after 48 hours from administration. The internal organs looked normal, except the internal wall of the jejunum which was colored yellow; this indicated still the existence of the drug within the villi.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A salt of the structural formula

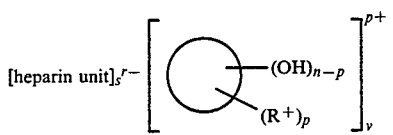
(I)

wherein ○ is the skeleton of a polyol, said polyol being a monosaccharide selected from the group consisting of pentoses, hexoses and heptoses, an oligosaccharide selected from the group consisting of disaccharides, trisaccharides and cyclodextrins, a $C_3$–$C_{15}$ aliphatic polyhydroxy compound of a $C_5$–$C_{18}$ alicyclic polyhydroxy compound, said skeleton being the portion of said polyol remaining after removal of all hydroxy substituents therefrom; n is a number from 3 to 24 which represents the total number of hydroxy groups in said polyol; p is a number $\geq 3$ and $\leq n$; r is the available valence of the heparin unit and is $\geq 3$ and $\leq 7$; s is the number which when multiplied by r is equal to pv; v is the number which when multiplied by p is equal to rs; $R^+$ is

(a)

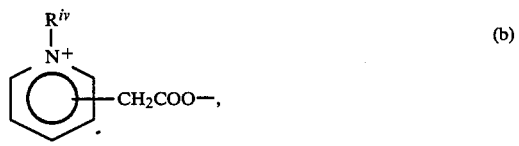
(b)

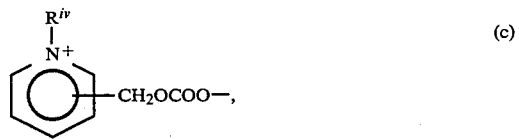
(c)

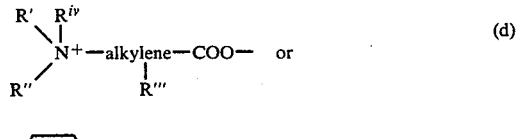
(d)

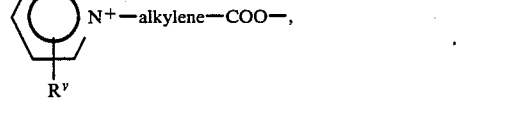
(e)

wherein the —COO—, —CH$_2$COO—, —CH$_2$OCOO— and $R^v$ ring substituents can each be in the 2-, 3- or 4-position of the pyridinium ring; $R^{iv}$ is $C_1$–$C_3$ alkyl; R′ and R″, which can be the same or different, are each $C_1$–$C_7$ alkyl, or R′ and R″ are combined with the adjacent nitrogen atom such that

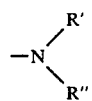

represents the residue of a saturated monocyclic secondary amine; R‴ is a radical identical to the corresponding portion of a natural amino acid; the alkylene groups can be straight or branched and contain 1 to 3 carbon atoms; and $R^v$ is H, —CONH$_2$ or —COO($C_1$–$C_7$ alkyl).

2. A salt as claimed in claim 1 wherein the polyol is ribose, arabinose, xylose, lyxose, ribulose, xylulose, glucose, galactose, mannose, fructose, sorbose, tagatose, mannoheptulose or sedoheptulose.

3. A salt as claimed in claim 1 wherein the oligosaccharide is sucrose, lactose, maltose, raffinose, α-cyclodextrin, β-cyclodextrin or γ-cyclodextrin.

4. A salt as claimed in claim 1 wherein the aliphatic polyhydroxy compound is a $C_3$–$C_8$ alkyl polyol.

5. A salt as claimed in claim 4 wherein the $C_3$–$C_8$ alkyl polyol is glycerol, erythritol or 1,2,6-trihydroxyhexane.

6. A salt as claimed in claim 1 wherein the alicyclic polyhydroxy compound is a $C_5$–$C_{10}$ cycloalkyl or fused fully hydrogenated aromatic polyol.

7. A salt as claimed in claim 6 wherein the cycloalkyl polyol is a cyclohexane polyol.

8. A salt as claimed in claim 7 wherein the cyclohexane polyol is inositol.

9. A salt as claimed in claim 6 wherein the fused fully hydrogenated aromatic polyol is a decahydronaphthalene polyol.

10. A salt as claimed in claim 1 wherein R‴ is H, —CH$_3$, —CH(CH$_3$)$_2$, —CH$_2$—CH(CH$_3$)$_2$,

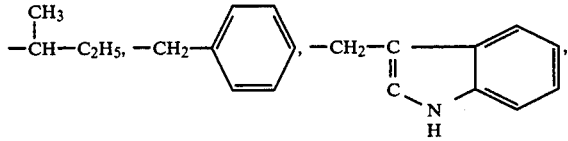

—CH$_2$OH, —CHOH—CH$_3$, —(CH$_2$)$_2$—SCH$_3$, —CH$_2$—CONH$_2$, —CH$_2$CH$_2$—CONH$_2$,

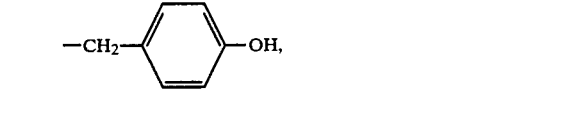

—CH$_2$SH, —CH$_2$COOH or —CH$_2$CH$_2$COOH.

11. A salt as claimed in claim 1 wherein R′ and R″ are combined with the adjacent nitrogen atom such that

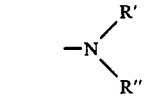

represents the residue of a saturated monocyclic secondary amine having 5 to 7 ring atoms, optionally containing another hetero ring atom —O—, —S— or —N— in addition to the indicated nitrogen atom, and optionally bearing 1 to 3 methyl substituents.

12. A salt as claimed in claim 11 wherein

is morpholino, 1-pyrrolidinyl, perhydro-1,2,4-oxathiazin-4-yl, 1- or 4-piperazinyl, 4-methyl-1-piperazinyl, piperidino, hexamethyleneimino, 2-methyl-1-pyrazolidinyl, 1- or 2-pyrazolidinyl, 3-methyl-1-imidazolidinyl or 1- or 3-imidazolidinyl.

13. A salt as claimed in claim 1 wherein $R^+$ is structure (a), (b) or (c); $R^{iv}$ is methyl; and the —COO—, —CH$_2$COO— or —CH$_2$OCOO— group is located in the 3-position.

14. A salt as claimed in claim 1 wherein $R^+$ is structure (d); R' is methyl or ethyl and R" is identical to R', or R'R"N— represents morpholino, piperidino, 1-pyrrolidinyl or 1-piperazinyl; $R^{iv}$ is methyl; and alkylene is —CH—.

15. A salt as claimed in claim 14 wherein R''' is H, —CH$_3$, —CH(CH$_3$)$_2$, —CH$_2$—CH(CH$_3$)$_2$,

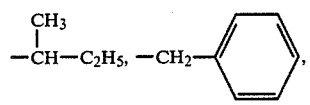

—(CH$_2$)$_2$—SCH$_3$, —CH$_2$—CONH$_2$, —CH$_2$CH$_2$—CONH$_2$ or

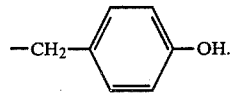

16. A salt as claimed in claim 1 wherein $R^+$ is structure (e) and alkylene is —CH$_2$— or —CH$_2$CH$_2$—.

17. A multiplet as claimed in claim 16 wherein $R^v$ is H or —CONH$_2$.

18. A salt as claimed in claim 1 wherein p is equal to n.

19. A salt as claimed in claim 1 wherein p is at least 4.

20. A salt as claimed in claim 1 wherein r is 5, 6 or 7.

21. A salt as claimed in claim 1 wherein ○ is the skeleton of inositol, n is 6 and p is 6.

22. A salt as claimed in claim 21 wherein v is 5, r is 5 and s is 6.

23. A salt as claimed in claim 22 having the structural formula

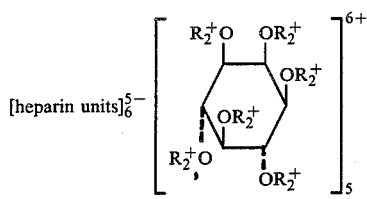

wherein $R_2^+$ is

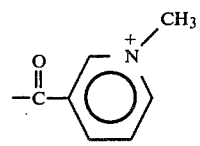

24. A salt of the structural formula

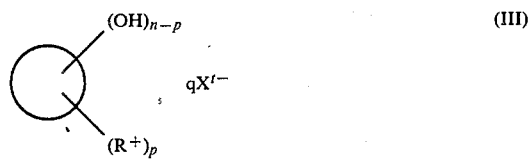

wherein ○ is the skeleton of a polyol, said polyol being a monosaccharide selected from the group consisting of pentoses, hexoses and heptoses, an oligosaccharide selected from the group consisting of disaccharides, trisaccharides and cyclodextrins, a C$_3$–C$_{15}$ aliphatic polyhydroxy compound or a C$_5$–C$_{18}$ alicyclic polyhydroxy compound, said skeleton being the portion of said polyol remaining after removal of all hydroxy substituents therefrom; n is a number from 3 to 24 which represents the total number of hydroxy groups in said polyol; p is a number $\geq 3$ and $\leq n$; $R^+$ is

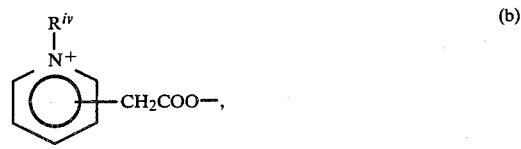

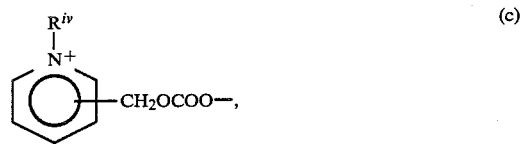

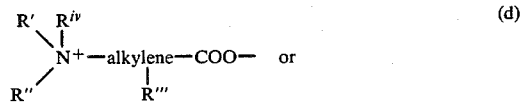

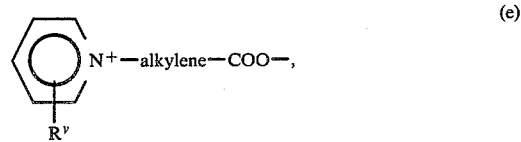

wherein the —COO—, —CH$_2$COO—, —CH$_2$OCOO— and $R^v$ ring substituents can each be in the 2-, 3- or 4-position of the pyridinium ring; $R^{iv}$ is C$_1$–C$_3$ alkyl; R' and R", which can be the same or different, are each C$_1$–C$_7$ alkyl, or R' and R" are combined with the adjacent nitrogen atom such that

represents the residue of a saturated monocyclic monocyclic secondary amine; R''' is a radical identical to the corresponding portion of a natural amino acid; the alkylene groups can be straight or branched and contain 1 to 3 carbon atoms; $R^v$ is H, —CONH$_2$ or —COO(C$_1$-C$_7$ alkyl); X$^-$ is the anion of a pharmaceutically acceptable organic or inorganic acid; t is the valence of the acid anion; and q is the number which when multiplied by t is equal to p.

25. A salt as claimed in claim 24 wherein the polyol is ribose, arabinose, xylose, lyxose, ribulose, xylulose, glucose, galactose, mannose, fructose, sorbose, tagatose, mannoheptulose or sedoheptulose.

26. A salt as claimed in claim 24 wherein the oligosaccharide is sucrose, lactose, maltose, raffinose, α-cyclodextrin, β-cyclodextrin or γ-cyclodextrin.

27. A salt as claimed in claim 24 wherein the aliphatic polyhydroxy compound is a C$_3$-C$_8$ alkyl polyol.

28. A salt as claimed in claim 27 wherein the C$_3$-C$_8$ alkyl polyol is glycerol, erythritol or 1,2,6-trihydroxyhexane.

29. A salt as claimed in claim 24 wherein the alicyclic polyhydroxy compound is a C$_5$-C$_{10}$ cycloalkyl or fused fully hydrogenated aromatic polyol.

30. A salt as claimed in claim 29 wherein the cycloalkyl polyol is a cyclohexane polyol.

31. A salt as claimed in claim 30 wherein the cyclohexane polyol is inositol.

32. A salt as claimed in claim 29 wherein the fused fully hydrogenated aromatic polyol is a decahydronaphthalene polyol.

33. A salt as claimed in claim 24 wherein R''' is H, —CH$_3$, —CH(CH$_3$)$_2$, —CH$_2$—CH(CH$_3$)$_2$,

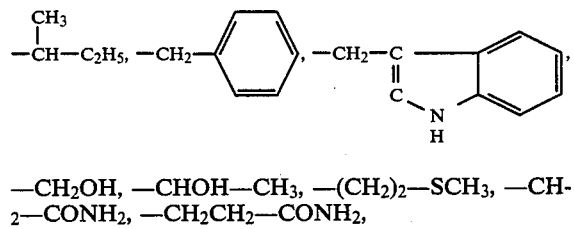

—CH$_2$OH, —CHOH—CH$_3$, —(CH$_2$)$_2$—SCH$_3$, —CH$_2$—CONH$_2$, —CH$_2$CH$_2$—CONH$_2$,

—CH$_2$SH, —CH$_2$COOH or —CH$_2$CH$_2$COOH.

34. A salt as claimed in claim 24 wherein R' and R'' are combined with the adjacent nitrogen atom such that

represents the residue of a saturated monocyclic secondary amine having 5 to 7 ring atoms, optionally containing another hetero ring atom —O—, —S— or —N— in addition to the indicated nitrogen atom, and optionally bearing 1 to 3 methyl substituents.

35. A salt as claimed in claim 34 wherein

is morpholino, 1-pyrrolidinyl, perhydro-1,2,4-oxathiazin-4-yl, 1- or 4-piperazinyl, 4-methyl-1-piperazinyl, piperidino, hexamethyleneimino, 2-methyl-1-pyrazolidinyl, 1- or 2-pyrazolidinyl, 3-methyl-1-imidazolidinyl or 1- or 3-imidazolidinyl.

36. A salt as claimed in claim 24 wherein R$^+$ is structure (a), (b) or (c); R$^{iv}$ is methyl; and the —COO—, —CH$_2$COO— or —CH$_2$OCOO— group is located in the 3-position.

37. A salt as claimed in claim 24 wherein R$^+$ is structure (d); R' is methyl or ethyl and R'' is identical to R', or R'R''N— represents morpholino, piperidino, 1-pyrrolidinyl or 1-piperazinyl; R$^{iv}$ is methyl; and alkylene is

38. A salt as claimed in claim 37 wherein R''' is H, —CH$_3$, —CH(CH$_3$)$_2$, —CH$_2$—CH(CH$_3$)$_2$,

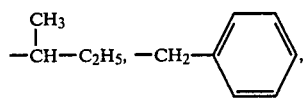

—(CH$_2$)$_2$—SCH$_3$, —CH$_2$—CONH$_2$, —CH$_2$CH$_2$—CONH$_2$ or

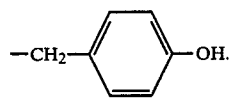

39. A salt as claimed in claim 24 wherein R$^+$ is structure (e) and alkylene is —CH$_2$— or —CH$_2$CH$_2$—.

40. A salt as claimed in claim 39 wherein R$^v$ is H or —CONH$_2$.

41. A salt as claimed in claim 24 wherein p is equal to n.

42. A salt as claimed in claim 24 wherein p is at least 4.

43. A salt as claimed in claim 24 wherein t is 1.

44. A salt as claimed in claim 24 wherein X$^-$ is I$^-$, Br$^-$ or Cl$^-$.

45. A salt as claimed in claim 24 wherein  is the skeleton of inositol, n is 6 and p is 6.

46. A salt as claimed in claim 45, having the structural formula

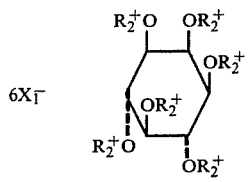

wherein $X_1^-$ is $I^-$, $Br^-$ or $Cl^-$ and $R_2^+$ is

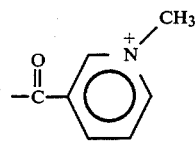

47. A salt as claimed in claim 46 wherein $X_1^-$ is $I^-$.

48. A method for eliciting an anticoagulant response in a warm-blooded animal, said method comprising orally administering to said animal an effective anticoagulant amount of a salt of formula (I) as defined by claim 1.

49. A method for eliciting an anticoagulant response in a warm-blooded animal, said method comprising administering to said animal nasally or by oral inhalation an effective anticoagulant amount of a salt of formula (I) as defined by claim 1.

50. A pharmaceutical composition of matter, in unit dosage form, for use in eliciting an anticoagulant response in a warm-blooded animal, said composition comprising, per dosage unit, an effective unit anticoagulant amount of a salt of formula (I) as defined by claim 1 and a non-toxic pharmaceutically acceptable carrier therefor.

51. A pharmaceutical composition as claimed in claim 50, suitable for oral administration.

52. A pharmaceutical composition as claimed in claim 50, suitable for nasal administration.

53. A pharmaceutical composition as claimed in claim 50, suitable for oral inhalation therapy.

* * * * *